(12) United States Patent
Uemoto et al.

(10) Patent No.: US 7,875,625 B2
(45) Date of Patent: Jan. 25, 2011

(54) CYCLOHEPTA[B]PYRIDINE-3-CARBONYLGUANIDINE DERIVATIVE AND PHARMACEUTICAL PRODUCT CONTAINING SAME

(75) Inventors: Kazuhiro Uemoto, Saitama (JP); Koichi Takayanagi, Saitama (JP); Shin-ichi Kazayama, Saitama (JP)

(73) Assignee: Toa Eiyo Ltd., Tokyo (JP)

( * ) Notice: Subject to any disclaimer, the term of this patent is extended or adjusted under 35 U.S.C. 154(b) by 539 days.

(21) Appl. No.: 11/816,420

(22) PCT Filed: Feb. 16, 2006

(86) PCT No.: PCT/JP2006/302713

§ 371 (c)(1),
(2), (4) Date: Aug. 16, 2007

(87) PCT Pub. No.: WO2006/088080

PCT Pub. Date: Aug. 24, 2006

(65) Prior Publication Data

US 2009/0012114 A1    Jan. 8, 2009

(30) Foreign Application Priority Data

Feb. 16, 2005   (JP)   ............... 2005-038780

(51) Int. Cl.
| | |
|---|---|
| C07D 221/04 | (2006.01) |
| A61K 31/435 | (2006.01) |
| A61P 35/00 | (2006.01) |
| A61P 3/10 | (2006.01) |
| A61P 9/10 | (2006.01) |
| A61P 9/06 | (2006.01) |

(52) U.S. Cl. ...................... 514/299; 546/112
(58) Field of Classification Search ............ 514/299; 546/112
See application file for complete search history.

(56) References Cited

U.S. PATENT DOCUMENTS

| | | | |
|---|---|---|---|
| 5,373,024 A | 12/1994 | Lang et al. | |
| 5,753,680 A | 5/1998 | Gericke et al. | |
| 6,258,829 B1 * | 7/2001 | Takahashi et al. | 514/335 |
| 6,350,749 B1 | 2/2002 | Shiraishi et al. | |
| 2003/0018056 A1 | 1/2003 | Kitano et al. | |

FOREIGN PATENT DOCUMENTS

| | | |
|---|---|---|
| JP | 5-339228 | 12/1993 |
| JP | 8-073427 | 3/1996 |
| JP | 8 208602 | 8/1996 |
| JP | 11 286454 | 10/1999 |
| JP | 2000-191641 | 7/2000 |
| WO | 98 39300 | 9/1998 |
| WO | 9839300 * | 9/1998 |
| WO | WO 01/44186 | 6/2001 |

OTHER PUBLICATIONS

Yaamamoto, Takeshi et al.,"Quantitative Structure-Activity Relationship Study of N-(3-Oxo-3,4-dihydro-2H-benzo [ 1,4] thiazine-6-carbonyl)guanidines as Potent Na/H Exchange Inhibitors", Chem. Pharm. Bull., vol. 48, No. 6, pp. 843-849, 2000.

(Continued)

Primary Examiner—D. Margaret Seaman
Assistant Examiner—Niloofar Rahmani
(74) Attorney, Agent, or Firm—Oblon, Spivak, McClelland, Maier & Neustadt, L.L.P.

(57) ABSTRACT

The present invention relates to a medicine, particularly a medicine comprising a novel cyclohepta[b]pyridine-3-carbonylguanidine derivative having an inhibitory effect on an $Na^+/H^+$ exchanger (NHE). There is provided a cyclohepta[b]pyridine-3-carbonylguanidine derivative represented by Formula (1):

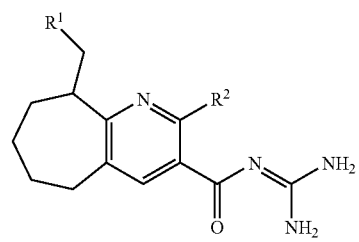

(1)

wherein $R^1$ is a group selected from a sulfo group, a sulfoxy group, $—OCONH—(CH_2CH_2O)_n—SO_3H$ and the following formulas:

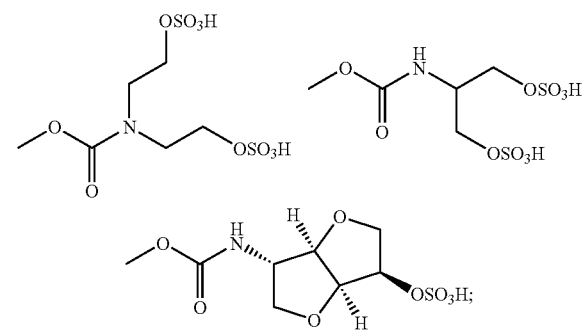

$R^2$ represents a halogen atom, a lower alkyl group or a lower alkoxy group; and n represents an integer from 1 to 10, or a pharmaceutically acceptable salt thereof.

6 Claims, No Drawings

OTHER PUBLICATIONS

Duff, et al., "Amiloride, Antiarrhythmic and Electrophysiologic Actions in Patients With Inducible Sustained Ventricular Tachycardia", Circulation, vol. 79, pp. 1257-1263, 1989.

Journal of Molecular Cell Cardiology, vol. 24, (Supplement I), S.92, 1992.

Touret, et al., "Characterization of sabiporide, a new specific NHE-1 inhibitor exhibiting slow dissociation kinetics and cardioprotective effects", European Journal of Pharmacology, vol. 459, pp. 151-158, 2003.

Cox, et al., "Sodium/Hydrogen Exchanger Gene Defect in Slow-Wave Epilepsy Mutant Mice", Cell, vol. 91, pp. 139-148, 1997.

* cited by examiner

CYCLOHEPTA[B]PYRIDINE-3-CARBONYLGUANIDINE DERIVATIVE AND PHARMACEUTICAL PRODUCT CONTAINING SAME

TECHNICAL FIELD

The present invention relates to a medicine, and in particular, to a novel cyclohepta[b]pyridine-3-carbonylguanidine derivative having an inhibitory effect on an $Na^+/H^+$ exchanger (NHE), and a medicine containing the same.

BACKGROUND ART

Ischemic myocardium undergoes virtually no histological changes when reperfused in the early phase of ischemia; however, when ischemia is sustained and reperfusion occurs during the course of necrosis, reperfusion injuries such as reperfusion-induced arrhythmia, no-reflow phenomenon and myocardial necrosis, which are mainly caused by $Ca^{2+}$ overload, are observed. If these reperfusion injuries could be suppressed to be minimal, it would be expected that such prevention would lead to an improved mortality or improved post-infarction cardiac function.

The NHE on the cell membrane is an ion transporter which controls the pH inside a cell by permitting a $Na^+$ influx into the cell and pumping $H^+$ out of the cell, and increased activity of the NHE is believed to cause the $Ca^{2+}$ overload during ischemic reperfusion. It is therefore conceived that an NHE inhibitor suppresses the $Ca^{2+}$ overload, thereby suppressing the ventricular fibrillation caused by reperfusion-induced arrhythmia and suppressing expansion of myocardial necrosis.

Furthermore, it is also suggested that NHE is involved in ischemia or ischemic reperfusion injury in various organs such as brain, liver and kidney in addition to the heart, as well as in hypertension, angina pectoris, cardiac hypertrophy, diabetes mellitus, diseases caused by proliferability of cells, or diseases caused by vascular endothelial disorder. Therefore, an NHE inhibitor is expected to be effective in suppressing these diseases or disorders, and is considered to be useful as a therapeutic agent or prophylactic agent of these diseases or disorders.

Amiloride, a $K^+$ sparing diuretic represented by the formula shown below, is a pyrazine derivative having acylguanidine. This derivative has NHE inhibitory effect, and is also reported to exhibit antiarrhythmic effect (Non-Patent Document 1). However, the antiarrhythmic effect of amiloride is weak, and also, amiloride has antihypertensive effect and salt excreting effect, which are rather considered as side effects that are undesirable for the treatment of arrhythmia.

[Chemical Formula 1]

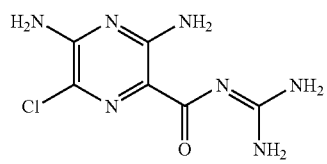

As a derivative which is not associated with the salt excreting effect, but has NHE inhibitory effect and antiarrhythmic effect, a benzoylguanidine derivative (Non-Patent Document 2, Patent Documents 1 and 2), an indolylguanidine derivative (Patent Document 3), an aminoguanidinehydrazone derivative (Patent Document 4), and a cycloalka[b]pyridine derivative (Patent Document 5) have been respectively reported.

In recent years, it has been reported that when the NHE inhibitor passes through the blood brain barrier and arrives at the brain, it manifests characteristic neurotoxicity which commonly appears in specific areas (Non-Patent Document 3). It is also reported that a NHE1 gene-deficient mouse displays severe ataxia, and neuropathy that is specific to cerebellum, vestibular nucleus and cochlear nucleus (Non-Patent Document 4). Therefore, the neurotoxicity of conventional NHE inhibitors has potential to induce various neuropathies. Accordingly, development of an NHE inhibitor which does not affect neurons is desired.

In Patent Document 6, introducing a —$SO_3H$ group (sulfo group), a —$PO_3H_2$ group or the like to the NHE inhibitors via various crosslinking groups has been suggested as a method of reducing the effect of the NHE inhibitors on the nervous system, particularly on the central nervous system, and specifically, the case of an indolylguanidine derivative is disclosed. However, since no specific data is presented for the effect of such introduction, the effectiveness of the introduction has been not proved for all conventional NHE inhibitors.

In fact, the inventors of the present invention have synthesized and investigated a variety of derivatives, and found that depending on the combination of the substituent and the NHE inhibitor as a nucleus, in some cases the NHE inhibitory effect has been significantly attenuated, or in some cases the derivative has been metabolized immediately after administration to be converted to the original NHE inhibitor, or in some cases, even the derivative itself has been exhibited an action on the central nervous system. Thus, such derivatives are not necessarily effective in reducing toxicity to the central nervous system.

[Patent Document 1] Japanese Patent Application Laid-open No. 5-339228

[Patent Document 2] Japanese Patent Application Laid-open No. 8-073427

[Patent Document 3] Japanese Patent Application Laid-open No. 8-208602

[Patent Document 4] Japanese Unexamined Patent Application No. 2000-191641

[Patent Document 5] International Patent Application Publication WO 98/39300

[Patent Document 6] International Patent Application Publication 01/044186

[Non-Patent Document 1] Circulation, Vol. 79, p. 1257-1263 (1989)

[Non-Patent Document 2] Journal of Molecular Cell Cardiology, Vol. 24 (suppl. I), S. 92 (1992)

[Non-Patent Document 3] European Journal of Pharmacology, Vol. 459, p. 151-158 (2003)

[Non-Patent Document 4] Cell, Vol. 91, p. 139-148 (1997)

DISCLOSURE OF THE INVENTION

Problems to be Solved by the Invention

An object of the present invention is to provide a low molecular weight compound which has an inhibitory effect on NHE, and is useful as a pharmaceutical product with reduced toxic effects on the central nervous system.

Means for Solving the Problems

In regard to such phenomenon, the inventors have devotedly investigated on NHE inhibitors having reduced toxic effects on the central nervous system, and as a result, found that a compound obtained by substituting the hydroxyl group on the methyl group at the 9-position of 9-hydroxymethyl-cyclohepta[b]pyridine-3-carbonylguanidine derivative with a specific substituent, exhibits an excellent NHE inhibitory effect in vitro as well as in vivo, while it is unlikely to undergo degradation to the original 9-hydroxymethyl product in the blood, and has extremely reduced toxic effect on the central nervous system due to low transferability to the brain.

Thus, the present invention relates to a cyclohepta[b]pyridine-3-carbonylguanidine derivative represented by Formula (1):

[Chemical Formula 2]

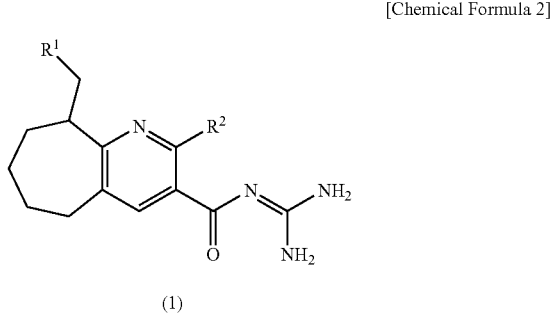

(1)

wherein $R^1$ represents a group selected from a sulfo group, a sulfoxy group, —OCONH—$(CH_2CH_2O)_n$—$SO_3H$ and the following formulas:

[Chemical Formula 3]

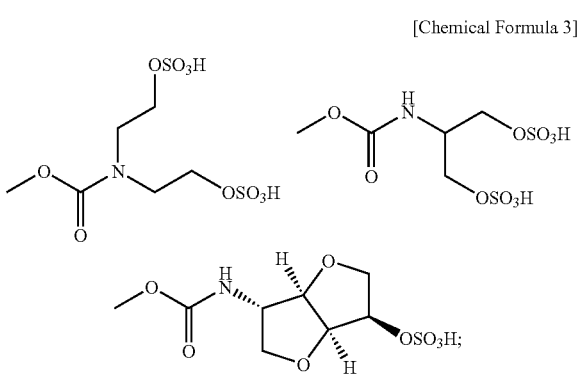

$R^2$ represents a halogen atom, a lower alkyl group or a lower alkoxy group; and n represents an integer from 1 to 10, or a pharmaceutically acceptable salt thereof, and to a medicine containing the same.

Another object of the invention is to provide a pharmaceutical composition containing the cyclohepta[b]pyridine-3-carbonylguanidine derivative represented by the Formula (1) or a pharmaceutically acceptable salt thereof, and a pharmaceutically acceptable carrier.

Another object of the invention is to provide the use of the cyclohepta[b]pyridine-3-carbonylguanidine derivative represented by the Formula (1) or a pharmaceutically acceptable salt thereof, for the manufacture of a medicine.

Yet another object of the invention is to provide a method for treating hypertension, arrhythmia, angina pectoris, cardiac hypertrophy, diabetes mellitus, organ disorder caused by ischemia or ischemic reperfusion, cerebral ischemic disorder, diseases caused by hyperproliferation of cells, or diseases caused by vascular endothelial cell disorder, including administering the cyclohepta[b]pyridine-3-carbonylguanidine derivative represented by the Formula (1) or a pharmaceutically acceptable salt thereof.

Effect of the Invention

The cyclohepta[b]pyridine-3-carbonylguanidine derivative represented by Formula (1) of the invention or a pharmaceutically acceptable salt thereof exhibits an excellent NHE inhibitory effect both in vitro and in vivo, while its toxic effect on the central nervous system is extremely low. Thus, the cyclohepta[b]pyridine-3-carbonylguanidine derivative represented by Formula (1) of the invention or a pharmaceutically acceptable salt thereof is useful as a medicine, particularly as a therapeutic agent or prophylactic agent for various diseases caused by stimulation of NHE, such as, for example, hypertension, arrhythmia, angina pectoris, cardiac hypertrophy, diabetes mellitus, organ disorder due to ischemia or ischemic reperfusion, cerebral ischemic disorder, diseases caused by hyperproliferation of cells, restenosis due to coronary endothelial thickening after percutaneous transluminal coronary angioplasty, and diseases caused by vascular endothelial cell disorder such as arteriosclerosis.

BEST MODE FOR CARRYING OUT THE INVENTION

For the cyclohepta[b]pyridine-3-carbonylguanidine derivative represented by Formula (1), when $R^1$ is —OCONH—$(CH_2CH_2O)_n$—$SO_3H$, n represents an integer from 1 to 10, and preferably 1 to 6.

$R^2$ represents a halogen atom, a lower alkyl group or a lower alkoxy group. The halogen atom may include a fluorine atom, a chlorine atom, a bromine atom and an iodine atom. The lower alkyl group includes a straight-chained or branched alkyl group having 1 to 6 carbon atoms, such as a methyl group, an ethyl group, a propyl group, an isopropyl group, a butyl group, an isobutyl group, a sec-butyl group and a tert-butyl group, and among these, a methyl group or an ethyl group is preferred, with a methyl group being particularly preferred. The lower alkoxy group includes a straight-chained or branched alkoxy group having 1 to 6 carbon atoms, such as a methoxy group, an ethoxy group, a propoxy group, an isopropoxy group, an n-butoxy group, a sec-butoxy group and a tert-butoxy group. $R^2$ is preferably a lower alkyl group, and most preferably a methyl group.

The present invention also encompasses pharmaceutically acceptable salts of the compound of Formula (1). Specific examples of these salts include salts with inorganic acids such as hydrochloride, hydrobromide, hydroiodide, sulfate and nitrate, phosphate; salts with organic acids such as acetic acid, trifluoroacetic acid, oxalic acid, fumaric acid, maleic acid, tartaric acid, mesylate and tosylate; salts with alkali metals, such as sodium salts and potassium salts; salts with alkaline earth metals, such as calcium salts; and the like, and these salts can be obtained by treating the present compound with an inorganic acid, an organic acid or the like according to a conventional method.

The compound (1) of the invention can exist as an optical isomer based on asymmetric carbon atoms. The present invention encompasses an isolated form of these various isomers as well as a mixture of these isomers. Also, the compound (1) of the invention encompasses a hydrate and various solvates.

Furthermore, the compound of the invention encompasses all of crystalline forms thereof.

Specific examples of the compound (1) of the present invention include:

3-guanidinocarbonyl-2-methyl-6,7,8,9-tetrahydro-5H-cyclohepta[b]pyridin-9-ylmethyl hydrogen sulfate, 3-guanidinocarbonyl-2-methyl-6,7,8,9-tetrahydro-5H-cyclohepta[b]pyridin-9-ylmethanesulfonic acid, 2-(3-guanidinocarbonyl-2-methyl-6,7,8,9-tetrahydro-5H-cyclohepta[b]pyridin-9-yl methyloxycarbonylamino) ethyl hydrogen sulfate, 2-[2-(3-guanidinocarbonyl-2-methyl-6,7,8,9-tetrahydro-5H-cyclohepta[b]pyridine-9-ylmethyloxycarbonylamino) ethoxy]ethyl hydrogen sulfate, 17-(3-guanidinocarbonyl-2-methyl-6,7,8,9-tetrahydro-5H-cyclohepta[b]pyridin-9-ylmethyloxycarbonylamino)-3,6,9,12,15-pentaoxaheptadecan-1-yl hydrogen sulfate 2-(3-guanidinocarbonyl-2-methyl-6,7,8,9-tetrahydro-5H-cyclohepta[b]pyridin-9-ylmethyloxycarbonylamino)-[N-(2-sulfoxyethyl)]ethyl hydrogen sulfate, 2-deoxy-1,4:3,6-dianhydro-2-(3-guanidinocarbonyl-2-methyl-6,7,8,9-tetrahydro-5H-cyclohepta[b]pyridin-9-ylmethyloxycarbonylamino)-D-glucitol-5-yl hydrogen sulfate, and pharmaceutically acceptable salts thereof.

Among these, preferred includes 3-guanidinocarbonyl-2-methyl-6,7,8,9-tetrahydro-5H-cyclohepta[b]pyridin-9-ylmethyl hydrogen sulfate, 3-guanidinocarbonyl-2-methyl-6,7,8,9-tetrahydro-5H-cyclohepta[b]pyridin-9-ylmethanesulfonic acid, 2-(3-guanidinocarbonyl-2-methyl-6,7,8,9-tetrahydro-5H-cyclohepta[b]pyridin-9-ylmethyloxycarbonylamino)ethyl hydrogen sulfate, and 2-[2-(3-guanidinocarbonyl-2-methyl-6,7,8,9-tetrahydro-5H-cyclohepta[b]pyridin-9-ylmethyloxycarbonylamino) ethoxy]ethyl hydrogen sulfate, and pharmaceutically acceptable salts thereof.

If $R^1$ in the Formula (1) is a sulfoxy group, the compound of the Formula (1) of the invention can be produced according to the reaction scheme as shown below:

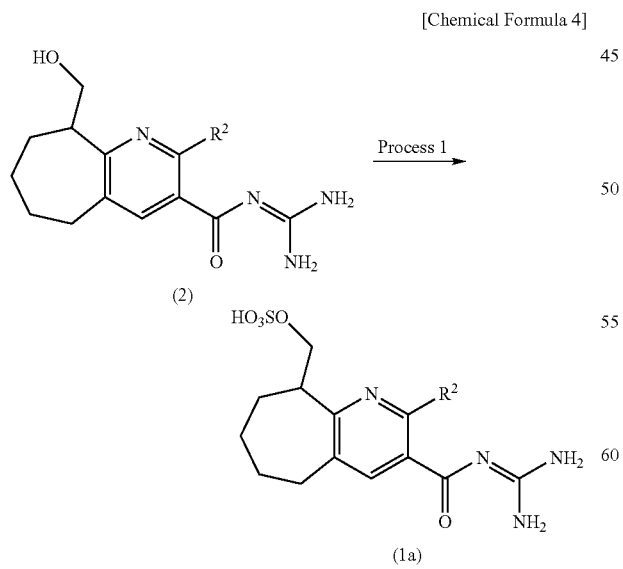

wherein $R^2$ has the same meaning as defined above.

Hereinafter, Process 1 will be described.

Process 1

The present process is a process for producing a compound represented by Formula (1a) by subjecting the primary hydroxyl group of a compound represented by Formula (2) to a sulfuric acid esterification reaction. That is, the compound of Formula (1a) can be obtained by reacting the compound of Formula (2) using a sulfuric acid esterifying agent such as chlorosulfonic acid, concentrated sulfuric acid, sulfur trioxide or sulfur trioxide-pyridine complex, in an organic solvent such as chloroform, dichloromethane, dimethylformamide (hereinafter, abbreviated to DMF), diethyl ether or tetrahydrofuran (hereinafter, abbreviated to THF), or without solvent, in the presence or absence of tertiary amine such as pyridine, triethylamine, dimethylaniline or dimethylaminopyridine, at a temperature of 0 to 40° C. for 1 to 24 hours.

In addition, the compound of Formula (2) can be obtained by, for example, subjecting a cycloalka[b]pyridine derivative to a heating reaction with guanidine, according to the method disclosed in WO 98/39300.

If $R^1$ in the Formula (1) is a sulfo group, the compound of the Formula (1) of the present invention can be produced according to, for example, the reaction scheme as shown below:

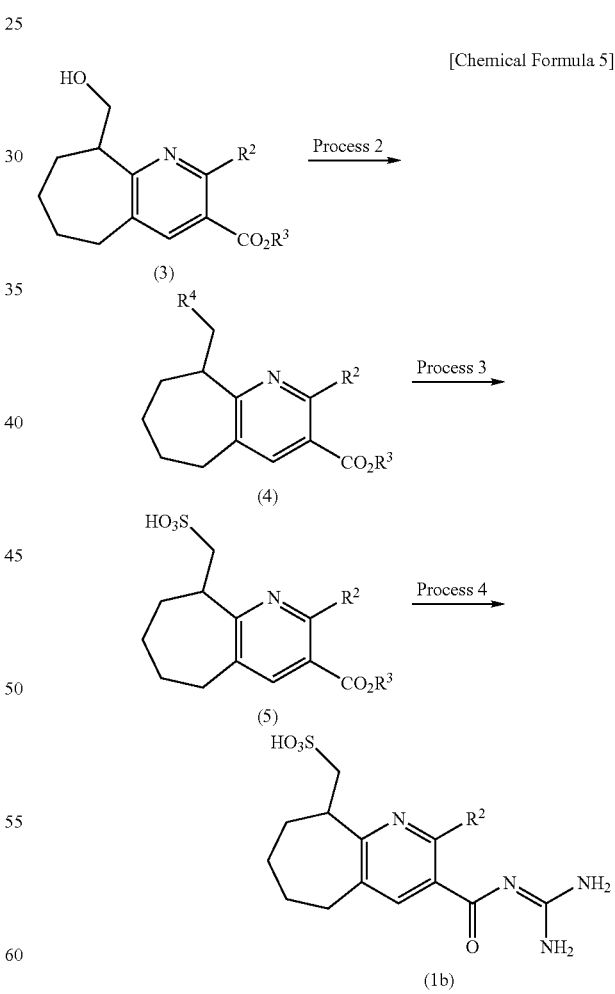

wherein $R^2$ has the same meaning as defined above; $R^3$ represents a lower alkyl group; and $R^4$ represents a halogen atom.

The definition for the lower alkyl group of $R^3$ or the halogen atom of $R^4$ is the same as in the case of $R^2$.

Hereinafter, Processes 2 to 4 will be described.

Process 2

The present process is a process for producing a compound represented by Formula (4) by converting the hydroxyl group of a compound of Formula (3) to a leaving group $R^4$. That is, the compound of Formula (4) can be obtained by reacting the compound of Formula (3) using a chlorinating agent such as thionyl chloride or phosphorus oxychloride, or using a brominating agent such as phosphorus tribromide or triphenylphosphine-carbon tetrabromide, in an organic solvent such as chloroform, dichloromethane, benzene, toluene, acetonitrile, DMF, diethyl ether or THF, or without solvent, in the presence or absence of tertiary amine such as pyridine, triethylamine, dimethylaniline or dimethylaminopyridine, at a temperature from −20° C. to the boiling temperature for 1 to 48 hours.

In addition, the compound of Formula (3) can be obtained by, for example, subjecting a cycloalka[b]pyridine derivative to a heating reaction with paraformaldehyde in a sealed tube according to the method disclosed in WO 98/39300.

Process 3

The present process is a process for producing a compound represented by Formula (5) by converting the leaving group $R^4$ of the compound of Formula (4) to sulfonic acid. That is, a compound of Formula (5) can be obtained by reacting the compound of Formula (4) using a sulfonating agent such as sodium sulfite or ammonium sulfite, in a hydrophilic solvent such as methanol, ethanol, n-propanol, acetone or DMF, or in a solvent mixture with water, or in water, at a temperature from room temperature to the boiling point for 1 to 48 hours.

Process 4

The present process is a process for producing a compound represented by Formula (1b) by converting the ester group of the compound of Formula (5) to a guanidinocarbonyl group. That is, the compound of Formula (1b) can be obtained by reacting a compound of Formula (6) with guanidine in an organic solvent such as methanol, ethanol, DMF, diethyl ether, THF or 1,4-dioxane, or without solvent, at a temperature from 0 to 100° C. for 1 to 24 hours.

Furthermore, in the case where $R^1$ in the Formula (1) represents $-OCONH-(CH_2CH_2O)_n-SO_3H$ or the following formula:

[Chemical Formula 6]

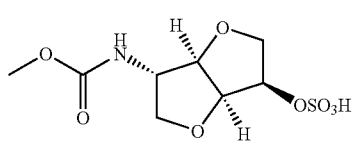

the compound of Formula (1) of the present invention can be produced, for example, according to the following reaction scheme:

[Chemical Formula 7]

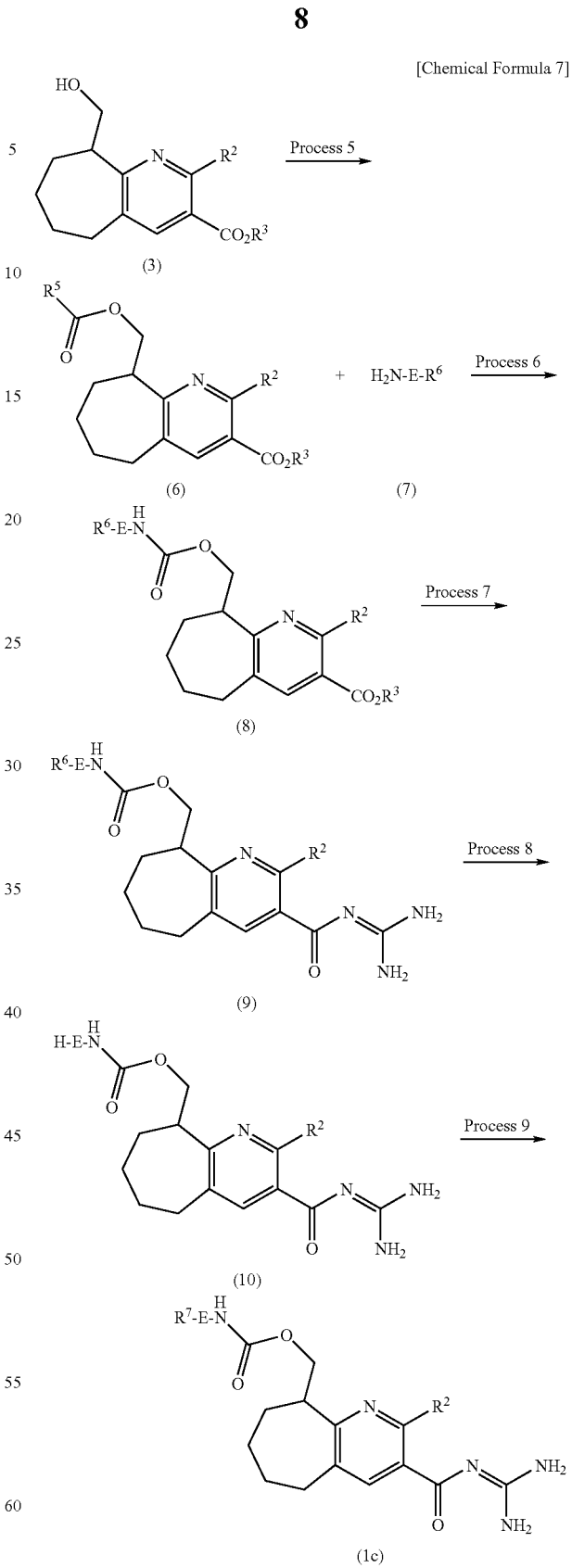

wherein $R^2$, $R^3$ and n have the same meanings as defined above; E represents $-(CH_2CH_2O)_n-$ or the following formula:

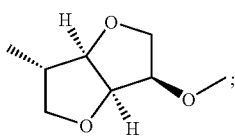

[Chemical Formula 8]

R⁵ represents a leaving group; R⁶ represents a hydrogen atom or a protective group for a hydroxyl group; and R⁷ represents a sulfo group.

The leaving group for R⁵ includes a 4-nitrophenoxy group, an imidazolyl group and the like, and the protective group for R⁶ includes a trisubstituted silyl group, a benzyl group and the like.

In addition, when R⁶ is a hydrogen atom, the Process 8 is not carried out. Hereinafter, the Processes 5 to 9 will be described.

Process 5

The present process is a process for producing a compound represented by Formula (6) by subjecting the primary hydroxyl group of the compound represented by Formula (3) to an active esterification reaction. That is, the compound of Formula (6) can be obtained by reacting the compound of Formula (3) using an active esterifying agent such as 4-nitrophenyl chlorocarbonate or 1,1'-carbonyldiimidazole, in an organic solvent such as chloroform, dichloromethane, DMF, diethyl ether or THF, or without solvent, in the presence or absence of tertiary amine such as pyridine, triethylamine, dimethylaniline or dimethylaminopyridine, at a temperature from 0 to 40° C. for 1 to 24 hours.

Process 6

The present process is a process for producing a compound represented by Formula (8) by reacting the active ester compound represented by Formula (6) with a primary amine represented by Formula (7). That is, the compound of Formula (8) can be obtained by reacting the compound of Formula (6) with the primary amine represented by Formula (7) in an organic solvent such as chloroform, dichloromethane, DMF, diethyl ether or THF, or without solvent, in the presence or absence of tertiary amine such as pyridine, triethylamine, dimethylaniline or dimethylaminopyridine, at a temperature from 0 to 40° C. for 1 to 24 hours.

In addition, the compound of Formula (7) wherein E is —(CH₂CH₂O)ₙ—, can be obtained as a commercially available reagent, or obtained from an ethylene glycol derivative according to, for example, the method disclosed in Tetrahedron Letters, Vol. 42, p. 3819-3822 (2001). In the case where E represents the following formula:

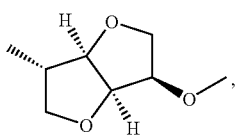

[Chemical Formula 9]

the compound can be obtained, for example, according to the method disclosed in EP0044927, by converting a hydroxyl group of isomannide to a leaving group, and then subjecting the product to a nucleophilic substitution reaction using aqueous ammonia.

Process 7

The present process is a process for producing a compound represented by Formula (9) by converting the ester group of the compound represented by Formula (8) to a guanidinocarbonyl group. That is, the compound of Formula (9) can be obtained by reacting the compound of Formula (8) using guanidine in an organic solvent such as methanol, ethanol, DMF, diethyl ether, THF or 1,4-dioxane, or without solvent, at a temperature from 0 to 100° C. for 1 to 24 hours.

Process 8

The present process is a process for producing a compound represented by Formula (10) by deprotecting the protective group for the hydroxyl group R⁶ of the compound represented by Formula (9). For example, when the protective group is a trisubstituted silyl group, the compound of Formula (10) can be obtained by reacting the compound of Formula (9) with hydrogen fluoride, tetrabutylammonium fluoride or the like in an organic solvent such as THF, at a temperature from 0 to 40° C. for 1 to 24 hours. When the protective group is a benzyl group, well-known methods such as catalytic reduction may be used. That is, the compound of Formula (10) can be obtained by reacting the compound of Formula (9) using a transition metal catalyst such as palladium carbon, palladium black, tris(triphenylphosphine) rhodium chloride or platinum oxide, in an organic solvent such as methanol, ethanol, 1,4-dioxane or DMF, at a temperature from 0 to 10° C. under ambient pressure or moderate hydrogen pressure for 1 to 24 hours.

Process 9

The present process is a process for producing a compound represented by Formula (1c) by subjecting the hydroxyl group of the compound represented by Formula (10) to a sulfuric acid esterification reaction. That is, the compound of Formula (1c) can be obtained by reacting the compound of Formula (10) using a sulfuric acid esterifying agent such as chlorosulfonic acid, concentrated sulfuric acid, sulfur trioxide or sulfur trioxide-pyridine complex, in an organic solvent such as chloroform, dichloromethane, DMF, diethyl ether or THF, or without solvent, in the presence or absence of tertiary amine such as pyridine, triethylamine, dimethylaniline or dimethylaminopyridine, at a temperature from 0 to 40° C. for 1 to 24 hours.

Furthermore, in the case where R¹ in the Formula (1) represents —OCONH—(CH₂CH₂O)ₙ—SO₃H or any of the following formulas:

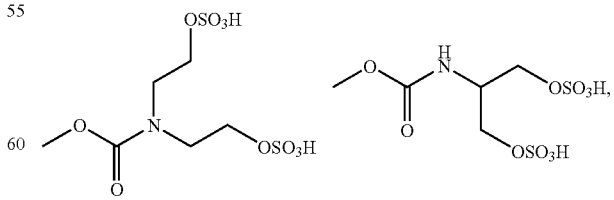

[Chemical Formula 10]

the compound of Formula (1) of the present invention can be produced according to the following reaction scheme as shown below.

[Chemical Formula 11]

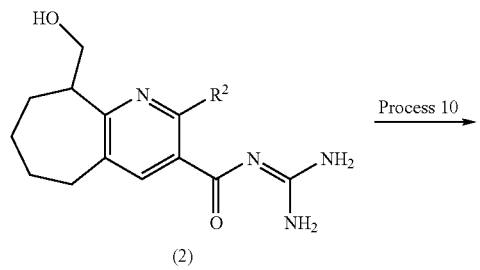
(2)

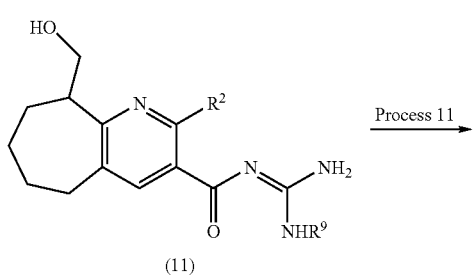
(11)

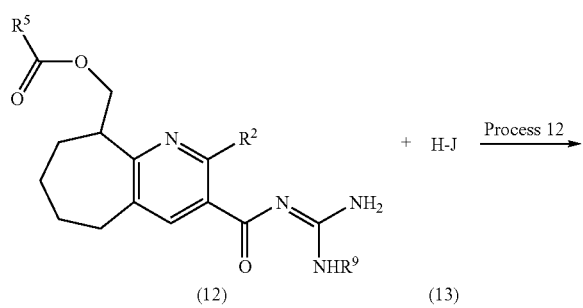
(12)          (13)

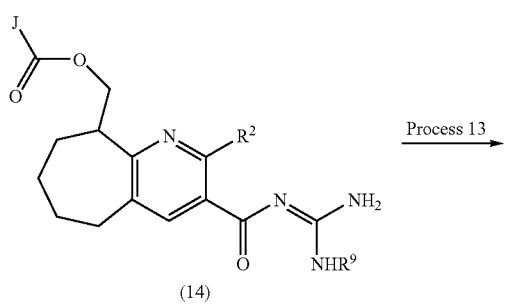
(14)

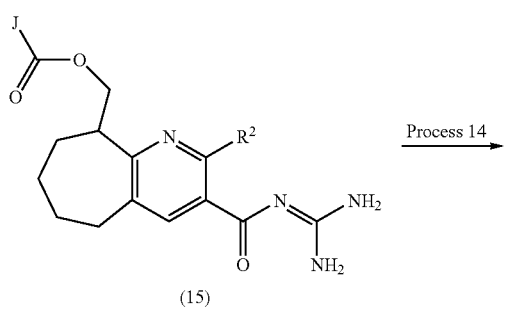
(15)

Process 10 →

Process 11 →

+ H-J  Process 12 →

Process 13 →

Process 14 →

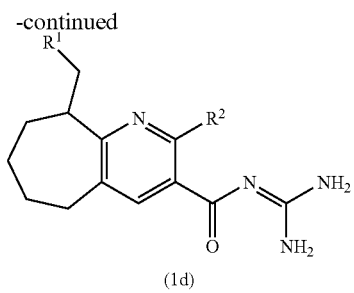
(1d)

wherein $R^2$, $R^5$ and n have the same meanings as defined above; $R^9$ represents a protective group for a guanidino group; and J represents —NH—$(CH_2CH_2O)_nH$ or the following formula:

[Chemical Formula 12]

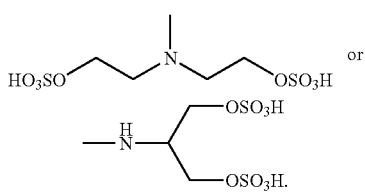

The protective group for $R^9$ includes a tert-butoxycarbonyl (hereinafter, abbreviated to Boc) group, a benzyloxycarbonyl (hereinafter, abbreviated to Z) group, and the like.

In addition, if J is a compound represented by Chemical Formula 12, the Process 14 is not carried out.

Hereinafter, the Processes 10 to 14 will be described.

Process 10

The present process is a process for producing a compound represented by Formula (11) by protecting the guanidino group of the compound represented by Formula (2) with, for example, a Boc group, a Z group or the like. In any case, the process can be carried out by a known method. For example, in the case where the protective group is a Boc group, the compound of Formula (11) can be obtained by reacting the compound of Formula (2) with di-tert-butyl dicarbonate, 2-(tert-butoxycarbonyloxyimino)-2-phenylacetonitrile or the like, in a solvent such as 1,4-dioxane, DMF or water or in a mixed solvent, in the presence or absence of a base such as sodium hydroxide or sodium hydrogen carbonate, at a temperature from 0 to 80° C. for 1 to 24 hours. In the case where the protective group is a Z group, the compound of Formula (11) can be obtained by reacting the compound of Formula (2) with benzyloxycarbonyl chloride or the like, in a solvent such as 1,4-dioxane, DMF or water or in a mixed solvent, in the presence or absence of a base such as sodium hydroxide or sodium hydrogen carbonate, at a temperature from 0 to 40° C. for 1 to 24 hours.

Process 11

The present process is a process for producing a compound represented by Formula (12) by subjecting the primary hydroxyl group of the compound represented by Formula (11) to an active esterification reaction. That is, the compound of Formula (12) can be obtained by reacting the compound of Formula (11) using an active esterifying agent such as 4-nitrophenyl chlorocarbonate or 1,1'-carbonyldiimidazole, in an organic solvent such as chloroform, dichloromethane, DMF, diethyl ether or THF, or without solvent, in the presence or absence of tertiary amine such as pyridine, triethylamine, dimethylaniline or dimethylaminopyridine, at a temperature from 0 to 40° C. for 1 to 24 hours.

Process 12

The present process is a process for producing a compound represented by Formula (14) by reacting the active ester compound represented by Formula (12) with an amine represented by Formula (13) or a salt thereof. That is, the compound of Formula (14) can be obtained by reacting the compound of Formula (12) with the amine represented by Formula (13) or a salt thereof, in an organic solvent such as chloroform, dichloromethane, DMF, diethyl ether or THF, or without solvent, in the presence or absence of tertiary amine such as pyridine, triethylamine, dimethylaniline or dimethylaminopyridine, at a temperature from 0 to 40° C. for 1 to 24 hours.

In addition, the compound of Formula (13) or a salt thereof, for example, when J represents —NH—(CH$_2$CH$_2$O)$_n$H, can be obtained according to the method described in The Journal of organic Chemistry, Vol. 66, p. 4494-4503 (2001) or in Tetrahedron Letters, Vol. 24, p. 1609-1610 (1983). Furthermore, if J represents the following formula:

[Chemical Formula 13]

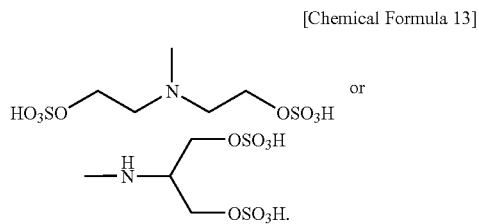

the compound of Formula (13) can be obtained according to the method described in Journal of the American Chemical Society, Vol. 75, p. 4101-4102 (1953), by performing sulfuric acid esterification of diethanolamine and serinol using chlorosulfonic acid, and then forming a salt therefrom, if necessary.

Process 13

The present process is a process for producing a compound represented by Formula (15) by deprotecting the protective group of the compound represented by Formula (14). The deprotection can be carried out by a known method. For example, when the protective group is a Boc group, the compound of Formula (15) can be obtained by reacting the compound of Formula (14) in an organic solvent such as methanol, ethanol, 1,4-dioxane or ethyl acetate, under acidic conditions in the presence of hydrogen chloride, trifluoroacetic acid or the like, at a temperature from 0 to 40° C. for 1 to 24 hours. When the protective group is a Z group, well-known methods such as catalytic reduction may be used. That is, the compound of Formula (15) can be obtained by reacting the compound of Formula (14) using a transition metal catalyst such as palladium carbon, palladium black, tris(triphenylphosphine) rhodium chloride or platinum oxide, in an organic solvent such as methanol, ethanol, 1,4-dioxane or DMF, at a temperature from 0 to 100° C. under ambient pressure or moderate hydrogen pressure for 1 to 24 hours.

Process 14

The present process is a process for producing a compound represented by Formula (1d) by subjecting the hydroxyl group of the compound represented by Formula (15) to a sulfuric acid esterification reaction. That is, the compound of Formula (1d) can be obtained by reacting the compound of Formula (15) using a sulfuric acid esterifying agent such as chlorosulfonic acid, concentrated sulfuric acid, sulfur trioxide or sulfur trioxide-pyridine complex, in an organic solvent such as chloroform, dichloromethane, DMF, diethyl ether or THF, or without solvent, in the presence or absence of tertiary amine such as pyridine, triethylamine, dimethylaniline or dimethylaminopyridine, at a temperature from 0 to 40° C. for 1 to 24 hours.

The compound of Formula (1) thus produced can be isolated and purified by conventionally used techniques such as recrystallization and column chromatography.

The cyclohepta[b]pyridine-3-carbonylguanidine derivative represented by Formula (1) of the present invention or a pharmaceutically acceptable salt thereof exhibits an excellent NHE inhibitory effect in vitro as well as in vivo, as will be described hereinafter in Test Examples, while having extremely low toxic effects on the central nervous system. Therefore, the cyclohepta[b]pyridine-3-carbonylguanidine derivative represented by Formula (1) of the invention or a pharmaceutically acceptable salt thereof is useful as a medicine, particularly as a therapeutic agent or prophylactic agent for various diseases caused by stimulation of NHE, such as for example, hypertension, arrhythmia, angina pectoris, cardiac hypertrophy, diabetes mellitus, organ disorder due to ischemia or ischemic reperfusion (for example, organ disorder due to myocardial ischemia reperfusion, acute renal failure, organ transplantation, percutaneous transluminal coronary angioplasty (PTCA), etc.), cerebral ischemic disorder (for example, injury associated with cerebral infarction, injury occurring as sequelae of cerebral apoplexy, cerebral edema, etc.), diseases caused by hyperproliferation of cells (for example, fibroblast proliferation, smooth muscle cell proliferation, mesangial cell proliferation, etc.) such as, atherosclerosis, pulmonary fibrosis, hepatic fibrosis, renal fibrosis, renal glumerulosclerosis, organomegaly, prostatic hypertrophy, diabetic complications, post-PTCA restenosis, etc., or restenosis due to coronary endothelial thickening after percuataneous transluminal coronary angioplasty, diseases caused by vascular endothelial cell disorder such as arteriosclerosis, and the like.

In the case of using the compound of Formula (1) of the present invention or a salt thereof as a medicine, the medicine can be administered orally or parenterally. The dosage form can contain pharmaceutically acceptable additives such as excipients, binding agents, buffering agents, thickening agents, stabilizing agents, emulsifying agents, dispersants, suspending agents and preservatives, and can be prepared by conventionally used methods.

Examples of the preparation for oral administration include tablets (including sugar-coated tablets and film-coated tablets), pills, granules, powders, capsules (including soft capsules), syrups, emulsions, suspensions and the like. These preparations for oral administration can be prepared by incorporating additives that are conventionally used in the field of pharmaceutics, according to known methods. Examples of such additives include excipients such as lactose, mannitol and anhydrous calcium hydrogen phosphate; binding agents such as hydroxypropylcellulose, methylcellulose and polyvinylpyrrolidone; disintegrants such as starch and carboxymethylcellulose; lubricants such as magnesium stearate and talc; and the like.

Parenteral administration can be performed by means of injectable preparations, rectal preparations, topical preparations and the like, and among these, injectable preparations are preferred. The injectable preparation includes a sterilized solution or suspension, and the like. Such injectable preparations are prepared, for example, by dissolving or suspending the compound of Formula (1) or a pharmaceutically acceptable salt thereof in the water for injection specified in the Japanese Pharmacopeia. If necessary, isotonic agents such as sodium chloride; buffering agents such as sodium dihydrogen phosphate and sodium hydrogen phosphate; dissolution aids; and the like may be incorporated. The preparation can also be prepared as dissolution-upon-use type (powder filled, freeze-dried) injectable preparations. In this case, excipients such as mannitol and lactose are added, and the preparations can be prepared by conventional methods.

The rectally administered preparation includes suppositories and the like. A suppository is produced, for example, by dissolving or suspending the compound of Formula (1) or a pharmaceutically acceptable salt thereof in a base material such as cacao butter or macrogol, and then pouring the solution or suspension in a mold to be molded. Furthermore, liquid or cream may be charged in an infusion container, and then used as a rectally administered preparation.

The topical preparation includes liquid preparations, eye-drops, creams, ointments, gel preparations, spray preparations, powder preparations and the like. The liquid preparation can be prepared by adding the compound of Formula (1) or a pharmaceutically acceptable salt thereof in water, and optionally adding stabilizing agents, solubilizing agents, thickening agents, dispersants, suspending agents and the like. As the thickening agent, gelatin, sodium hyaluronate, high molecular weight dextran, sodium alginate, sodium chondroitin sulfate, and the like may be used. The eye-drop can be prepared by adding preservatives, in addition to buffering agents, pH adjusting agents, isotonic agents and the like. The cream and ointment can be prepared using aqueous or oil-based base materials, such as water, liquid paraffin, plant oils (peanut oil, castor oil, etc.) and macrogol. The gel preparation can be prepared by a known method, using gelatin, pectin, carrageenan, agar, tragacanth gum, alginates, cellulose ether (methylcellulose, sodium carboxymethylcellulose, etc.), pectin derivatives, polyacrylate, polymethacrylate, polyvinyl alcohol, polyvinylpyrrolidone and the like. The spray preparation can be prepared by dissolving or suspending the compound of Formula (1) or a pharmaceutically acceptable salt thereof in water or the like, and then filling the solution or suspension into a spray container. In the case of a powder preparation, the compound of Formula (1) or a pharmaceutically acceptable salt thereof can be used as it is, or else, the preparation can be prepared by mixing the compound with suitable excipients.

The daily dose of the compound represented by Formula (1) for an adult may vary depending on the symptoms, body weight, or age of patient, type of the compound, administration route, or the like, but in the case of oral administration, the dose is suitably about 0.01 to 1,000 mg, and preferably about 0.1 to 300 mg. In the case of parenteral administration, an amount of one-tenth to a half of the dosage for oral administration may be administered. These doses can be appropriately increased or decreased in accordance with the symptoms, body weight, age or the like of patient.

EXAMPLES

Hereinafter, the present invention will be described in more detail with reference to Reference Examples and Examples, but the present invention is not intended to be limited thereto.

Reference Example 1

2-Formylcycloheptanone (Reference Compound 1)

In an argon atmosphere, sodium hydride (60%; 55.2 g, 1.38 mol) was suspended in ether (2 L), and ethanol (2.5 mL) was added thereto at room temperature. Then, a liquid mixture of cycloheptanone (141 g, 1.26 mol) and ethyl formate (152 mL, 1.84 mol) was added dropwise to the mixture over 2 hours, and the resulting mixture was stirred at the same temperature for 20 hours. Ethanol (25 mL) was added to the reaction solution, subsequently water (1.2 L) was added, and the mixture was separated. The resultant was extracted with a 10% (w/v) aqueous solution of sodium hydroxide, and then the aqueous layers were combined and washed with ether. 15% (v/v) hydrochloric acid was added to the aqueous layer under ice cooling to adjust the aqueous layer to pH 3 to 4, and then the mixture was extracted twice with ether, washed with saturated solution of sodium chloride, and then dried over anhydrous sodium sulfate. The solvent was evaporated under reduced pressure, and thus the title compound (174 g, 99%) was obtained as a pale orange oil.

IR (neat) 2927, 2853, 1645, 1584, 1452, 1435, 1406, 1255, 1220 $cm^{-1}$;

$^1$H-NMR (300 MHz, $CDCl_3$) δ: 14.67 (d, J=8.7 Hz, 1H), 7.64 (d, J=8.7 Hz, 1H), 2.56-2.52 (m, 2H), 2.28-2.24 (m, 2H), 1.79-1.58 (m, 6H).

Reference Example 2

Methyl 2-methyl-6,7,8,9-tetrahydro-5H-cyclohepta[b]pyridine-3-carboxylate (Reference Compound 2)

Reference Compound 1 (29.9 g, 214 mmol) and methyl 3-aminocrotonate (25.1 g, 218 mmol) were dissolved in acetic acid (30 mL), and the solution was stirred at 100° C. for 20 hours. The solvent was evaporated under reduced pressure, and the residue was neutralized with a saturated aqueous solution of sodium carbonate under ice cooling. The resultant was extracted twice with ethyl acetate, washed with water, a saturated aqueous solution of sodium hydrogen carbonate and saturated solution of sodium chloride, and dried over anhydrous magnesium sulfate. The solvent was evaporated under reduced pressure, and the residue was purified by distillation under reduced pressure (135-136° C., 1 mmHg), thus to obtain the title compound (32.4 g, 69%) as a pale yellow oil.

IR (neat) 2925, 2848, 1723, 1559, 1456, 1436, 1285, 1260, 1246, 1201, 1147, 1119, 1057, 783 $cm^{-1}$;

$^1$H-NMR (300 MHz, $CDCl_3$) δ: 7.89 (s, 1H), 3.89 (s, 3H), 3.06-3.02 (m, 2H), 2.81-2.77 (m, 2H), 2.76 (s, 3H), 1.91-1.84 (m, 2H), 1.73-1.64 (m, 4H).

Reference Example 3

Methyl 9-hydroxymethyl-2-methyl-6,7,8,9-tetrahydro-5H-cyclohepta[b]pyridine-3-carboxylate (Reference Material 3)

Reference Compound 2 (30.0 g, 137 mmol) and paraformaldehyde (24.6 g) were placed in a sealed tube made of iron, and the mixture was stirred at 120° C. for 24 hours. The reaction solution was extracted with 10% (v/v) hydrochloric acid, and washed with ether. A 40% (w/v) aqueous solution of sodium hydroxide was added to the aqueous layer under ice cooling to adjust the aqueous layer to pH 10, and the mixture was extracted twice with chloroform. The organic layer was washed with water and saturated solution of sodium chloride, and dried over anhydrous sodium sulfate. The solvent was evaporated under reduced pressure, and the residue was purified by silica gel column chromatography (hexane: ether=2:1 to 0:1), thus to obtain the title compound (13.4 g, 39%) as a colorless powder. Melting point: 55 to 56° C.;

IR (KBr) 3475, 3425, 2920, 2854, 1728, 1427, 1277, 1130, 1053 cm$^{-1}$;

$^1$H-NMR (300 MHz, CDCl$_3$) δ: 7.93 (s, 1H), 4.68 (br, 1H), 3.95 (d, J=2.5 Hz, 2H), 3.90 (s, 3H), 3.15-3.08 (m, 1H), 2.78 (s, 3H), 2.97-2.71 (m, 2H), 2.08-1.97 (m, 2H), 1.84-1.61 (m, 2H), 1.43-1.21 (m, 2H).

Reference Example 4

9-Hydroxymethyl-2-methyl-6,7,8,9-tetrahydro-5H-cyclohepta[b]pyridine-3-carbonylguanidine (Reference Compound 4)

In an argon atmosphere, a 28% (w/v) sodium methoxide/methanol solution (146 mL, 759 mmol) was added to a solution of guanidine hydrochloride (72.5 g, 759 mmol) in methanol (300 mL) under ice cooling, and the mixture was stirred at the same temperature for 1 hour. The mixture was filtered through a glass filter (G4) to remove any precipitate, and then the solvent was evaporated under reduced pressure. To a solution of the residue in DMF (120 mL), a solution of Reference Compound 3 (37.8 g, 152 mmol) in DMF (80 mL) was added, and the mixture was stirred at 80° C. for 1 hour. The solvent was evaporated under reduced pressure, the residue was azeotroped with toluene, water was added to the residue, and crystallization was performed. The precipitated powder was collected by filtration, washed with water and dried under reduced pressure, thus to obtain a crude product. Subsequently, the product was dissolved in chloroform-methanol (1:1) by heating to reflux, and then an ether solution of diazomethane was added dropwise to the solution under ice cooling, followed by stirring overnight. Diazomethane was distilled off by heating to reflux, and then the solvent was evaporated under reduced pressure. The residue was suspended in methanol and collected by filtration to obtain the title compound (32.2 g, 77%) as a colorless powder.

Melting point: 239-241° C.;

IR (KBr) 3402, 3132, 2927, 1651, 1597, 1527, 1331, 1053, 633 cm$^{-1}$;

$^1$H-NMR (300 MHz, DMSO-d$_6$) δ: 7.78 (s, 1H), 4.53-4.57 (m, 1H), 3.93-3.85 (m, 1H), 3.73-3.65 (m, 1H), 3.04-2.97 (m, 1H), 2.79-2.63 (m, 2H), 2.57 (s, 3H), 1.94-1.61 (m, 4H), 1.31-1.14 (m, 2H).

Reference Example 5

Methyl 9-bromomethyl-2-methyl-6,7,8,9-tetrahydro-5H-cyclohepta[b]pyridine-3-carboxylate (Reference Compound 5)

In an argon atmosphere, triphenylphosphine (9.48 g, 36.2 mmol) and carbon tetrabromide (16.00 g, 48.2 mmol) were added to a solution of Reference Compound 3 (6.01 g, 24.1 mmol) in dichloromethane (120 mL) under ice cooling, and the mixture was stirred at room temperature for 1.5 hours. The solvent was evaporated under reduced pressure, then a 50% saturated aqueous solution of sodium hydrogen carbonate was added, and the mixture was extracted with diethyl ether: ethyl acetate (10:1). The organic layer was washed with saturated solution of sodium chloride and dried over anhydrous sodium sulfate. Subsequently, the solvent was evaporated under reduced pressure, and the residue was purified by silica gel column chromatography (hexane: diethyl ether=20:1 to 10:1), thus to obtain the title compound (6.74 g, 90%) as a colorless solid.

Melting point: 66-67° C.;

IR (KBr) 3420, 2988, 2922, 2853, 1721, 1595, 1557, 1455, 1436, 1397, 1372, 1280, 1245, 1199, 1185, 1129, 1080, 1051, 964, 941, 931, 877, 853, 785, 755, 669, 637, 598, 568 cm$^{-1}$;

$^1$H-NMR (300 MHz, CDCl$_3$) δ: 7.88 (s, 1H), 4.19 (dd, J=10.1, 4.7 Hz, 1H), 3.90 (s, 3H), 3.71 (t, J=10.1 Hz, 1H), 3.41-3.33 (m, 1H), 2.86-2.71 (m, 2H), 2.75 (s, 3H), 2.23-1.72 (m, 4H), 1.46-1.33 (m, 2H).

Reference Example 6

3-Methoxycarbonyl-2-methyl-6,7,8,9-tetrahydro-5H-cyclohepta[b]pyridin-9-ylmethanesulfonic acid (Reference Compound 6)

A solution of sodium sulfite (3.00 g, 23.8 mmol) in water (44.0 mL) was added to Reference Compound 5 (6.73 g, 21.6 mmol), and the mixture was heated to reflux for 6 hours. A solution of sodium sulfite (1.36 g, 10.8 mmol) in water (10.0 mL) was added to the mixture, and the resultant mixture was heated to reflux for another 5 hours, left to cool to room temperature and washed with diethyl ether. Hydrochloric acid (1 mol/L) was added in small amounts to the aqueous layer to adjust the aqueous layer to pH 2 to 3. The aqueous layer was washed with chloroform. The residual organic solvent was evaporated under reduced pressure, and the residue was purified by HP-20 (Mitsubishi Chemical Corp.) column chromatography (water to 50% methanol), thus to obtain the title compound (12.1 g, 56%) as a colorless solid.

Melting point: 262-263° C. (decomposition);

IR (KBr) 3423, 3033, 2942, 2856, 1710, 1647, 1600, 1438, 1395, 1287, 1231, 1191, 1153, 1125, 1031, 957, 779, 726, 666, 527 cm$^{-1}$;

$^1$H-NMR (300 MHz, DMSO-d$_6$) δ: 8.51 (s, 1H), 5.45 (brs, 1H), 3.90 (s, 3H), 3.86-3.84 (m, 1H), 3.26-3.19 (m, 1H), 3.02-2.89 (m, 3H), 2.83 (s, 3H), 1.95-1.72 (brm, 5H), 1.46-1.34 (brm, 1H).

Reference Example 7

Methyl 2-methyl-9-(4-nitrophenoxycarbonyloxymethyl)-6,7,8,9-tetrahydro-5H-cyclohepta[b]pyridine-3-carboxylate (Reference Compound 7)

To a solution of 4-nitrophenyl chlorocarbonate (1.21 g, 6.0 mmol) in dichloromethane (7.5 mL), a solution of Reference Compound 3 (1.25 g, 5.0 mmol) and pyridine (0.8 mL, 10 mmol) in dichloromethane (2.5 mL) was added in an ice bath, and the mixture was stirred at the same temperature for 2 hours. The reaction solution was diluted with chloroform, and then the dilution was washed with a saturated aqueous solution of sodium hydrogen carbonate and saturated solution of sodium chloride, and dried over anhydrous sodium sulfate. The solvent was evaporated under reduced pressure, and the residue was purified by silica gel column chromatography (hexane:ethyl acetate=6:1 to 1:2) and then recrystallized from ethyl acetate-hexane, thus to obtain the title compound (1.66 g, 80%) as a colorless powder.

Melting point: 116-117° C.;

IR (KBr) 2933, 2857, 1773, 1725, 1592, 1521, 1434, 1347, 1274, 1224, 1134, 1063, 966, 934, 862 cm$^{-1}$;

$^1$H-NMR (300 MHz, CDCl$_3$) δ: 8.28 (d, J=9.2 Hz, 2H), 7.91 (s, 1H), 7.39 (d, J=9.2 Hz, 2H), 5.09 (dd, J=10.8, 6.1 Hz, 1H), 4.58 (dd, J=10.8, 7.9 Hz, 1H), 3.90 (s, 3H), 3.46-3.38 (m, 1H), 2.95-2.77 (m, 2H), 2.74 (s, 3H), 2.08-1.97 (m, 3H), 1.89-1.75 (m, 1H), 1.45-1.25 (m, 2H).

Reference Example 8

Methyl 2-methyl-9-(2-hydroxyethylaminocarbonyloxymethyl)-6,7,8,9-tetrahydro-5H-cyclohepta[b]pyridine-3-carboxylate (Reference Compound 8)

In an argon atmosphere, Reference Compound 7 (1.00 g, 2.4 mmol) was added to a solution of ethanolamine (150 μL, 2.5 mmol) and triethylamine (1.0 mL, 7.2 mmoLmol) in dichloromethane (12 mL), and the mixture was stirred at room temperature for 24 hours. The reaction solution was diluted in chloroform, and the dilution was washed with water, a 1% (w/v) aqueous solution of sodium hydroxide, a saturated aqueous solution of ammonium chloride and saturated solution of sodium chloride. The dilution was dried over anhydrous sodium sulfate, and the solvent was evaporated under reduced pressure. The residue was purified by silica gel column chromatography (chloroform:methanol=100:1), thus to obtain the title compound (840 mg, quantitative) as colorless crystals.

Melting point: 111-112° C.;

IR (KBr) 3319, 2918, 2846, 1690, 1600, 1544, 1437, 1400, 1276, 1163, 1059, 998, 786, 670 cm$^{-1}$;

$^1$H-NMR (300 MHz, CDCl$_3$) δ: 7.87 (s, 1H), 5.05 (br, 1H), 4.81 (dd, J=11.0, 6.8 Hz, 1H), 4.40-4.34 (m, 1H), 3.89 (s, 3H), 3.76-3.69 (m, 2H), 3.39-3.25 (m, 3H), 2.83-2.77 (m, 2H), 2.74 (s, 3H), 2.21 (br, 1H), 2.03-1.70 (m, 4H), 1.50-1.29 (m, 2H).

Reference Example 9

2-Methyl-9-(2-hydroxyethylaminocarbonyloxymethyl)-6,7,8,9-tetrahydro-5H-cyclohepta[b]pyridine-3-carbonylguanidine (Reference Compound 9)

In an argon atmosphere, a 28% (w/v) solution of sodium methoxide/methanol (4.2 mL, 21.8 mmol) was added to a solution of guanidine hydrochloride (2.08 g, 21.7 mmol) in methanol (21.7 mL), and the mixture was stirred at room temperature for 1 hour. The precipitate was removed by filtering through a glass filter (G4), and then the solvent was evaporated under reduced pressure. To a solution of the residue in DMF (10 mL), a solution of Reference Compound 8 (730 mg, 2.2 mmol) in DMF (11.7 mL) was added, and the mixture was stirred for 1 hour at room temperature, and for another 1 hour at 60° C. The solvent was evaporated under reduced pressure, water was added to the residue, and the mixture was extracted with ethyl acetate. The organic layer was washed with saturated solution of sodium chloride and then dried over anhydrous sodium sulfate, and the solvent was evaporated under reduced pressure. The residue was purified by aminated silica gel column chromatography (chloroform:methanol=100:1 to 30:1), thus to obtain the title compound (386 mg, 49%) as a colorless amorphous material.

IR (KBr) 3358, 3228, 2927, 2846, 1701, 1637, 1598, 1523, 1442, 1414, 1359, 1262, 1153, 1069, 939, 893, 755 cm$^{-1}$;

$^1$H-NMR (300 MHz, DMSO-d$_6$) δ: 7.69 (s, 1H), 6.92 (t, J=5.7 Hz, 1H), 4.52-4.46 (m, 2H), 4.09 (t, J=10.6 Hz, 1H), 3.37-3.26 (m, 2H), 3.14-3.07 (m, 1H), 2.98-2.92 (m, 2H), 2.74-2.55 (m, 2H), 2.49 (s, 3H), 1.88-1.70 (m, 3H), 1.65-1.53 (m, 1H), 1.21-1.04 (m, 2H);

MS (ESI) m/z 364 (M+H)$^+$.

Reference Example 10

N-tert-Butoxycarbonyl-9-hydroxymethyl-2-methyl-6,7,8,9-tetrahydro-5H-cyclohepta[b]pyridine-3-carbonylguanidine (Reference Compound 10)

Di-tert-butyl dicarbonate (19 mL, 160 mmol) was added to a solution of Reference Compound 4 (22.1 g, 80 mmol) in DMF (240 mL), and the mixture was stirred at 60° C. for 2.5 hours. Di-tert-butyl dicarbonate (4.75 mL, 40 mmol) was further added, and the mixture was stirred at the same temperature for 3 hours. After standing the mixture to cool, the solvent was evaporated under reduced pressure, water was added to the residue, and the mixture was extracted with ethyl acetate. The organic layer was washed with saturated solution of sodium chloride and dried over anhydrous sodium sulfate. The solvent was evaporated under reduced pressure, and the residue was purified by silica gel column chromatography (hexane:ethyl acetate=3:1 to 2:1), crystallized from diethyl ether and collected by filtration. Thus, the title compound (27.4 g, 91%) was obtained as a colorless powder.

Melting point: 98 to 100° C.;

IR (KBr) 3361, 3221, 3110, 2971, 2929, 2880, 2852, 1725, 1637, 1591, 1542, 1458, 1395, 1369, 1304, 1244, 1151, 1029, 1018, 855, 838, 777, 752, 592 cm$^{-1}$.

$^1$H-NMR (300 MHz, CDCl$_3$) δ: 9.19 (br, 2H), 8.63 (br, 1H), 7.86 (s, 1H), 4.90 (br, 1H), 3.99 (d, J=5.5 Hz, 2H), 3.12-3.05 (m, 1H), 2.84-2.65 (m, 2H), 2.73 (s, 3H), 2.07-1.94 (m, 2H), 1.81-1.73 (m, 2H), 1.46 (s, 9H), 1.43-1.21 (m, 2H).

Reference Example 11

N-tert-Butoxycarbonyl-2-methyl-9-(4-nitrophenoxycarbonyloxymethyl)-6,7,8,9-tetrahydro-5H-cyclohepta[b]pyridine-3-carbonylguanidine (Reference Compound 11)

The title compound (16.0 g, 43%) was obtained, as a colorless powder, from Reference Compound 10 (26.0 g, 69 mmol) in the same manner as in Reference Example 7.

Melting point: 135-137° C.;

IR (KBr) 3438, 3320, 3122, 3086, 2979, 2921, 2850, 1764, 1722, 1635, 1585, 1523, 1491, 1439, 1388, 1348, 1322, 1214, 1148, 1014, 935, 883, 863, 765, 573 cm$^{-1}$;

$^1$H-NMR (300 MHz, CDCl$_3$) δ: 8.64 (br, 1H), 8.27 (d, J=9.2 Hz, 2H), 7.81 (s, 1H), 7.39 (d, J=9.2 Hz, 2H), 5.08 (dd, J=10.8, 6.0 Hz, 1H), 4.58 (dd, J=10.8, 8.0 Hz, 1H), 3.44-3.36

(m, 1H), 2.90-2.69 (m, 2H), 2.69 (s, 3H), 2.09-1.75 (m, 4H), 1.47 (s, 9H), 1.47-1.35 (m, 2H).

Reference Example 12

N-tert-Butoxycarbonyl-9-[2-(2-hydroxyethoxy)ethylaminocarbonyloxymethyl]-2-methyl-6,7,8,9-tetrahydro-5H-cyclohepta[b]pyridine-3-carbonylguanidine (Reference Compound 12)

In an argon atmosphere, Reference Compound 11 (541 mg, 1.0 mmol) was added to a solution of 2-(2-aminoethoxy)ethanol (0.10 mL, 1.0 mmol) and triethylamine (0.42 mL, 3.0 mmol) in DMF (10 mL), and the mixture was stirred at room temperature for 19 hours. The solvent was evaporated, and the residue was dissolved in chloroform, and washed with a 1% aqueous solution of sodium hydroxide, a saturated aqueous solution of ammonium chloride and saturated solution of sodium chloride. The solution was dried over anhydrous sodium sulfate, and then the solvent was evaporated under reduced pressure. The residue was purified by silica gel column chromatography (chloroform:methanol=20:1), thus to obtain the title compound (472 mg, 93%) as a colorless amorphous material.

IR (KBr) 3381, 2968, 2929, 2856, 1730, 1893, 1637, 1543, 1460, 1367, 1311, 1246, 1151, 1069, 1023, 893, 847, 781, 753 cm$^{-1}$;

$^1$H-NMR (300 MHz, CDCl$_3$) δ: 8.64 (br, 2H), 8.01 (s, 1H), 7.70 (s, 1H), 5.11 (brt, J=5.1 Hz, 1H), 4.79 (dd, J=10.7, 6.5 Hz, 1H), 4.34 (dd, J=10.7, 2.5 Hz, 1H), 3.73-3.70 (m, 2H), 3.55 (brm, 4H), 3.39-3.23 (m, 3H), 2.78-2.73 (m, 2H), 2.67 (s, 3H), 2.01-1.32 (m, 6H), 1.49 (s, 9H);

MS (ESI) m/z 508 (M+H)$^+$.

Reference Example 13

9-[2-(2-Hydroxyethoxy)ethylaminocarbonyloxymethyl]-2-methyl-6,7,8,9-tetrahydro-5H-cyclohepta[b]pyridine-3-carbonylguanidine (Reference Compound 13)

At room temperature, 1 mol/L hydrochloric acid (10 mL) was added to a solution of Reference Compound 12 (512 mg, 1.0 mmol) in methanol (10 mL), and the mixture was stirred for 20 hours. A 10% (w/v) aqueous solution of sodium hydroxide was added in small amounts to neutralize the mixture, and methanol was evaporated under reduced pressure. The aqueous layer was washed with chloroform and chloroform:methanol=30:1, and then the residual organic solvent was evaporated under reduced pressure. The residue was purified by HP-20 column chromatography (water to methanol), thus to obtain the title compound (274 mg, 67%) as a colorless amorphous material.

IR (KBr) 3358, 2926, 2856, 1700, 1637, 1598, 1526, 1439, 1414, 1351, 1272, 1123, 1066, 939, 893, 799, 771, 620 cm$^{-1}$;

$^1$H-NMR (300 MHz, CD$_3$OD) δ: 7.60 (s, 1H), 4.67 (dd, J=10.6, 5.5 Hz, 1H), 4.32 (dd, J=10.6, 9.1 Hz, 2H), 3.67-3.62 (m, 2H), 3.52-3.48 (brm, 4H), 3.34-3.27 (m, 3H), 2.83-2.80 (m, 2H), 2.57 (s, 3H), 2.03-1.75 (m, 4H), 1.49-1.35 (m, 2H);

MS (ESI) m/z 408 (M+H)$^+$.

Reference Example 14

Methyl 9-(17-tert-butyldiphenylsilyloxy-3,6,9,12,15-pentaoxaheptadecan-1-ylaminocarbonyloxymethyl)-2-methyl-6,7,8,9-tetrahydro-5H-cyclohepta[b]pyridine-3-carboxylate (Reference Compound 14)

The title compound (2.38 g, quantitative) was obtained, as a pale yellow oil, from 17-amino-1-tert-butyldiphenylsilyloxy-3,6,9,12,15-pentaoxaheptadecane (1.91 g, 3.0 mmol) and Reference Compound 7 (1.05 g, 3.1 mmol) in the same manner as in Reference Example 8.

IR (neat) 3355, 3070, 2929, 2856, 1714, 1597, 1556, 1538, 1469, 1432, 1350, 1283, 1247, 1112, 942, 823, 787, 743, 705, 614, 505 cm$^{-1}$;

$^1$H-NMR (300 MHz, CDCl$_3$) δ: 7.86 (s, 1H), 7.69-7.66 (m, 4H), 7.44-7.34 (m, 6H), 5.26 (br, 1H), 4.79 (dd, J=11.0, 5.7 Hz, 1H), 4.35 (dd, J=11.0, 8.4 Hz, 1H), 3.89 (s, 3H), 3.80 (t, J=5.4 Hz, 2H), 3.66-3.52 (m, 20H), 3.41-3.25 (m, 3H), 2.81-2.75 (m, 2H), 2.73 (s, 3H), 2.03-1.65 (m, 4H), 1.41-1.25 (m, 2H), 1.04 (s, 9H).

Reference Example 15

9-(17-tert-Butyldiphenylsilyloxy-3,6,9,12,15-pentaoxaheptadecan-1-ylaminocarbonyloxymethyl-2-methyl-6,7,8,9-tetrahydro-5H-cyclohepta[b]pyridine-3-carbonylguanidine (Reference Compound 15)

The title compound (288 mg, 69%) was obtained, as a yellow oil, from Reference Compound 14 (404 mg, 0.51 mmol) in the same manner as in Reference Example 9.

IR (neat) 3410, 3070, 2928, 2856, 1714, 1693, 1609, 1538, 1469, 1339, 1255, 1144, 1105, 1033, 949, 893, 823, 751, 706, 614 cm$^{-1}$;

$^1$H-NMR (300 MHz, DMSO-d$_6$) δ: 7.77 (s, 1H), 7.65-7.61 (m, 4H), 7.47-7.38 (m, 6H), 7.06 (t, J=5.5 Hz, 1H), 4.57 (dd, J=11.0, 5.0 Hz, 1H), 4.17 (dd, J=11.0, 8.8 Hz, 1H), 3.73 (t, J=4.8 Hz, 2H), 3.54-3.08 (m, 23H), 2.80-2.64 (m, 2H), 2.56 (s, 3H), 1.94-1.60 (m, 4H), 1.29-1.10 (m, 2H), 0.98 (s, 9H).

Reference Example 16

9-(17-Hydroxy-3,6,9,12,15-pentaoxaheptadecan-1-ylaminocarbonyloxymethyl-2-methyl-6,7,8,9-tetrahydro-5H-cyclohepta[b]pyridine-3-carbonylguanidine (Reference Compound 16)

In an argon atmosphere, a 1 mol/L tetrabutylammonium fluoride/THF solution (345 μL, 0.35 mmol) was added to a solution of Reference Compound 15 (286 mg, 0.35 mmol) in THF (3.5 mL) under ice cooling, and the mixture was stirred for 14 hours while allowing the temperature to freely rise to room temperature. After adding a saturated aqueous solution of ammonium chloride, the resultant mixture was extracted with ethyl acetate, and washed with saturated solution of sodium chloride. The mixture was dried over anhydrous sodium sulfate, and then the solvent was evaporated under reduced pressure. The residue was purified by aminated silica gel column chromatography (chloroform:methanol=120:1 to 100:1), thus to obtain the title compound (199 mg, 98%) as a colorless oil.

IR (neat) 3366, 2925, 2865, 1698, 1637, 1601, 1544, 1516, 1456, 1405, 1339, 1259, 1102, 942, 755 cm$^{-1}$;

$^1$H-NMR (300 MHz, CD$_3$OD) δ: 7.89 (s, 1H), 7.62 (s, 1H), 4.68 (dd, J=10.6, 5.3 Hz, 1H), 4.33 (dd, J=10.6, 8.8 Hz, 1H), 3.68-3.50 (m, 22H), 3.28-3.20 (m, 3H), 2.84-2.81 (m, 2H), 2.58 (s, 3H), 2.02-1.35 (m, 6H);

MS (ESI) m/z 584 (M+H)$^+$, 582 (M–H)$^-$.

Reference Example 17

2-Deoxy-1,4:3,6-dianhydro-2-(3-methoxycarbonyl-2-methyl-6,7,8,9-tetrahydro-5H-cyclohepta[b]pyridin-9-ylmethyloxycarbonylamino)-D-glucitol (Reference Compound 17)

The title compound (763 mg, 92%) was obtained, as a colorless amorphous material, from 2-amino-2-deoxy-1,4:3,6-dianhydro-D-glucitol (435 mg, 3.0 mmol) and Reference Compound 7 (819 mg, 2.0 mmol) in the same manner as in Reference Example 8.

IR (KBr) 3442, 3326, 2929, 2855, 1719, 1597, 1542, 1437, 1281, 1250, 1134, 1079, 1043, 786, 753 cm$^{-1}$;

$^1$H-NMR (300 MHz, CDCl$_3$) δ: 7.87 (s, 1H), 4.86-4.79 (m, 2H), 4.56-4.52 (m, 1H), 4.41-4.25 (m, 4H), 3.94-3.83 (m, 3H), 3.89 (s, 3H), 3.61 (dd, J=9.5, 5.5 Hz, 1H), 3.29 (d, J=5.5 Hz, 1H), 2.86-2.78 (m, 2H), 2.73 (s, 3H), 2.59 (d, J=6.8 Hz, 1H), 2.04-1.70 (m, 4H), 1.44-1.26 (m, 2H).

Reference Example 18

9-(2-Deoxy-1,4:3,6-dianhydro-D-glucitol-2-ylaminocarbonyloxymethyl)-2-methyl-6,7,8,9-tetrahydro-5H-cyclohepta[b]pyridine-3-carbonylguanidine (Reference Compound 18)

The title compound (662 mg, 84%) was obtained, as a colorless amorphous material, from Reference Compound 17 (744 mg, 1.77 mmol) in the same manner as in Reference Example 9.

IR (KBr) 3368, 2927, 1700, 1637, 1597, 1523, 1438, 1411, 1341, 1264, 1164, 1086, 1040, 881, 751 cm$^{-1}$;

$^1$H-NMR (300 MHz, DMSO-d$_6$) δ: 7.77 (s, 1H), 7.42 (d, J=4.8 Hz, 1H), 4.76 (d, J=6.2 Hz, 1H), 4.61 (dd, J=10.8, 5.5 Hz, 1H), 4.31 (s, 2H), 4.18 (dd, J=10.3, 9.5 Hz, 1H), 4.09-4.04 (m, 1H), 3.85-3.83 (m, 2H), 3.69 (t, J=7.5 Hz, 2H), 3.36-3.30 (m, H), 3.28-3.15 (m, 1H), 2.82-2.62 (m, 2H), 2.57 (s, 3H), 1.95-1.62 (m, 4H), 1.30-1.14 (m, 2H);

MS (ESI) m/z 448 (M+H)$^+$.

Reference Example 19

Dibenzyl(3-guanidinocarbonyl-2-methyl-6,7,8,9-tetrahydro-5H-cyclohepta[b]pyridin-9-ylmethyl) phosphate (Reference Compound 19)

To a suspension of Reference Compound 4 (553 mg, 2.0 mmol) in DMF (10 mL), dibenzyl-N,N'-diisopropylphosphoramidate (1.0 mL, 3.0 mmol) and 1H-tetrazole (322 mg, 4.6 mmol) were added in an ice bath, and the mixture was stirred at room temperature for 2 hours. Subsequently, m-chloroperbenzoic acid (70%; 740 mg, 3.0 mmol) was added thereto at −78° C., and the mixture was stirred at the same temperature for 10 minutes. Dichloromethane and a saturated aqueous solution of sodium hydrogen carbonate were added to the reaction solution to separate it. Then, the organic layer was washed with a saturated aqueous solution of sodium hydrogen carbonate and saturated solution of sodium chloride. After drying the organic layer over anhydrous sodium sulfate, the solvent was evaporated under reduced pressure, and the residue was purified by aminated silica gel column chromatography (chloroform:methanol=1:0 to 10:1), thus to obtain the title compound (531 mg, 49%) as a colorless amorphous material.

IR (KBr) 3393, 3219, 3065, 3033, 2925, 2852, 1637, 1597, 1523, 1457, 1438, 1418, 1339, 1250, 1013, 879, 802, 737, 697, 600, 497 cm$^{-1}$;

$^1$H-NMR (300 MHz, CDCl$_3$) δ: 7.42 (s, 1H), 7.40-7.29 (m, 10H), 5.10-4.77 (m, 5H), 4.15-4.08 (m, 1H), 3.42-3.35 (m, 1H), 2.86-2.65 (m, 2H), 2.53 (s, 3H), 1.81-1.57 (m, 6H);

MS (ESI) m/z 537 (M+H)$^+$.

Reference Example 20

3-Guanidinocarbonyl-2-methyl-6,7,8,9-tetrahydro-5H-cyclohepta[b]pyridin-9-ylmethyl phosphate disodium salt (Reference Compound 20)

5% (w/w) palladium carbon (230 mg) was added to a solution of Reference compound 19 (460 mg, 0.86 mmol) in methanol (10 mL), and the mixture was stirred in a hydrogen atmosphere at room temperature for 20 hours. Hydrochloric acid (1 mol/L) (5 mL) was added to the reaction solution, and then the mixture was filtered through Celite. A saturated aqueous solution of sodium hydrogen carbonate was added to the filtrate to neutralize the filtrate (pH 7). The precipitate was filtered and dried under reduced pressure to obtain a phosphoric acid monoester product. Subsequently, a 28% (w/v) sodium methoxide/methanol solution (0.14 mL) was added to a methanol suspension of the phosphoric acid monoester product, and the mixture was stirred for 5 hours. The solvent was evaporated under reduced pressure, and the residue was collected by filtration, thus to obtain the title compound (157 mg, 48%) as an ocher-colored powder.

Melting point: 254-256° C.;

IR (KBr) 3358, 2930, 2856, 2230, 1646, 1597, 1527, 1439, 1355, 1086, 980, 904, 801, 539, 480, 449 cm$^{-1}$;

$^1$H-NMR (300 MHz, D$_2$O) δ: 7.45 (s, 1H), 4.04-3.98 (m, 2H), 3.30-3.20 (m, 1H), 2.85-2.63 (m, 2H), 2.38 (s, 3H), 1.77-1.41 (m, 6H);

MS (ESI) m/z 357 (M+3H-2Na)$^+$.

Reference Example 21

2-Hydroxymethyl-6,7,8,9-tetrahydro-5H-cyclohepta-[b]pyridine-3-carbonylguanidine (Reference Compound 21)

The title compound (674 mg, 9%) was obtained, as a colorless amorphous material, from 6,7,8,9-tetrahydro-5H-cyclohepta[b]pyrido[3,2-c]furan-3-one (6.09 g, 30.0 mmol) in the same manner as in Reference Example 9.

IR (KBr) 3349, 3189, 2921, 1672, 1628, 1570, 1536, 1445, 1408, 1375, 1259, 1193, 1157, 1014, 992, 958, 892, 820 cm$^{-1}$;

$^1$H-NMR (300 MHz, DMSO-d$_6$) δ: 8.03 (s, 1H), 6.92 (br, 4H), 5.57 (t, J=4.2 Hz, 1H), 4.65 (d, J=4.2 Hz, 2H), 3.04-3.00 (m, 2H), 2.82-2.79 (m, 2H), 1.89-1.81 (m, 2H), 1.69-1.56 (m, 4H).

Reference Example 22

3-Guanidinocarbonyl-6,7,8,9-tetrahydro-5H-cyclohepta[b]pyridin-2-ylmethyl hydrogen sulfate (Reference Compound 22)

The title compound (396 mg, 58%) was obtained, as a colorless amorphous material, from Reference Compound 21 (524 mg, 2.00 mmol) in the same manner as in Example 1.

IR (KBr) 3474, 3353, 3207, 2933, 1665, 1625, 1541, 1449, 1426, 1380, 1270, 1223, 1068, 1016, 819, 739 cm$^{-1}$;

$^1$H-NMR (300 MHz, DMSO-d$_6$) δ: 8.20 (brs, 1H), 7.76 (br, 2H), 7.50 (br, 2H), 5.28 (brs, 2H), 3.19-3.16 (m, 2H), 2.94-2.92 (m, 2H), 1.91-1.82 (m, 2H), 1.73-1.58 (m, 4H).

Reference Example 23

3-Guanidinocarbonyl-2-methyl-6,7,8,9-tetrahydro-5H-cyclohepta[b]pyridin-5-yl hydrogen sulfate (Reference Compound 23)

The title compound (351 mg, 51%) was obtained, as a colorless amorphous material, from 5-hydroxy-2-methyl-6,7,8,9-tetrahydro-5H-cyclohepta[b]pyridine-3-carbonylguanidine (525 mg, 2.00 mmol) in the same manner as in Example 1.

IR (KBr) 3369, 3181, 2932, 1708, 1597, 1457, 1247, 1210, 1154, 1055, 986, 904, 857, 819 cm$^{-1}$;

$^1$H-NMR (300 MHz, DMSO-d$_6$) δ: 11.38 (br, 1H), 8.19 (br, 4H), 7.83 (s, 1H), 5.20 (d, J=9.2 Hz, 1H), 3.03-2.81 (m, 2H), 2.49 (s, 3H), 2.08-1.88 (m, 2H), 1.74-1.51 (m, 3H), 1.35-1.24 (m, 1H);

MS (ESI) m/z 341 (M−H)$^-$.

Example 1

3-Guanidinocarbonyl-2-methyl-6,7,8,9-tetrahydro-5H-cyclohepta[b]pyridin-9-ylmethyl hydrogen sulfate (Inventive Compound 1)

A sulfur trioxide-pyridine complex (11.0 g, 72 mmol) was added to a suspension of Reference Compound 4 (6.35 g, 23 mmol) in pyridine (115 mL), and the mixture was stirred at room temperature for 1 hour. The solvent was evaporated under reduced pressure, and the residue was azeotroped with toluene. Water was added to the residue, the mixture was stirred for 30 minutes, and then a precipitated powder was collected by filtration. Subsequently, water was added thereto, the mixture was heated to reflux for 1 hour, and then an insoluble powder was collected by filtration, thus to obtain the title compound (7.0 g, 85%) as a colorless powder.

Melting point: 231-233° C.;

IR (KBr) 3395, 3315, 3153, 2931, 2856, 1698, 1637, 1576, 1542, 1448, 1240, 1201, 1138, 1063, 976, 780, 748 cm$^{-1}$;

$^1$H-NMR (300 MHz, DMSO-d$_6$) δ: 11.30 (br, 1H), 8.12 (br, 4H), 7.68 (s, 1H), 4.25 (dd, J=10.5, 4.2 Hz, 1H), 3.90 (dd, J=10.5, 9.9 Hz, 1H), 3.23-3.17 (m, 1H), 2.85-2.69 (m, 2H), 2.49 (s, 3H), 2.03-1.58 (m, 4H), 1.28-1.01 (m, 2H).

Example 2

3-Guanidinocarbonyl-2-methyl-6,7,8,9-tetrahydro-5H-cyclohepta[b]pyridin-9-ylmethyl sulfate sodium salt (Inventive Compound 2)

To a suspension of the Inventive Compound 1 (8.91 g, 25 mmol) in water (50 mL), a 28% (w/v) sodium methoxide/methanol solution (4.83 mL) was added under ice cooling, and the mixture was stirred at the same temperature for 1 hour. The solvent was evaporated under reduced pressure, and the residue was purified by HP-20 column chromatography (water to 50% methanol), crystallized from ethanol and collected by filtration, thus to obtain the title compound (5.3 g, 50%) as a colorless powder.

Melting point: 222-223° C.;

IR (KBr) 3423, 2924, 2854, 1654, 1601, 1522, 1458, 1420, 1363, 1248, 1060, 979, 805 cm$^{-1}$;

$^1$H-NMR (300 MHz, D$_2$O) δ: 7.45 (s, 1H), 4.40 (dd, J=9.8, 7.6 Hz, 1H), 4.24 (dd, J=9.8, 8.2 Hz, 1H), 3.37-3.30 (m, 1H), 2.81-2.63 (m, 2H), 2.38 (s, 3H), 1.75-1.48 (m, 6H).

Example 3

3-Guanidinocarbonyl-2-methyl-6,7,8,9-tetrahydro-5H-cyclohepta[b]pyridin-9-ylmethanesulfonic acid (Inventive Compound 3)

In an argon atmosphere, a 28% (w/v) sodium methoxide/methanol solution (23.3 mL, 121 mmol) was added to a solution of guanidine hydrochloride (11.5 g, 121 mmol) in methanol (120 mL), and the mixture was stirred at room temperature for 1 hour. A precipitate was removed by filtering through a glass filter (G4), and the solvent was evaporated under reduced pressure. The residue was dissolved in DMF (50 mL), a solution of Reference Compound 6 (3.78 g, 12.1 mmol) in DMF (120 mL) was added thereto, and the mixture was stirred at room temperature for 12 hours. The solvent was evaporated under reduced pressure, then water (50 mL) was added to the residue, and 6 mol/L hydrochloric acid was added dropwise to adjust the mixture to pH 2. The resulting solution was purified by HP-20 column chromatography (water to 50% methanol), thus to obtain the title compound (2.12 g, 52%) as a colorless powder.

Melting point: 245-247° C.

IR (KBr) 3363, 3162, 2935, 2857, 1715, 1655, 1599, 1560, 1543, 1447, 1364, 1278, 1246, 1212, 1160, 1138, 1078, 1039, 960, 910, 877, 823, 790, 773, 755, 681, 585, 551, 524 cm$^{-1}$;

$^1$H-NMR (300 MHz, DMSO-d$_6$) δ: 11.37 (brs, 1H), 8.22 (br, 4H), 7.75 (brs, 1H), 3.49 (br, 1H), 3.21 (br, 1H), 2.92-2.67 (m, 4H), 2.57 (s, 3H), 2.39-2.27 (m, 1H), 1.97-1.67 (brm, 3H), 1.41-1.25 (brm, 1H);

MS (ESI) m/z 339 (M−H)$^-$.

Example 4

3-Guanidinocarbonyl-2-methyl-6,7,8,9-tetrahydro-5H-cyclohepta[b]pyridin-9-ylmethanesulfonic acid sodium salt (Inventive Compound 4)

The title compound (1.67 g, 83%) was obtained, as a colorless powder, from the Inventive Compound 3 (1.90 g, 5.58 mmol) in the same manner as in Example 2.

Melting point: 215-219° C.;

IR (KBr) 3400, 3219, 2926, 2856, 1637, 1599, 1523, 1439, 1414, 1356, 1191, 1045, 921, 875, 799, 596 cm$^{-1}$;

$^1$H-NMR (300 MHz, DMSO-d$_6$) δ: 7.9-6.5 (br, 4H), 7.76 (s, 1H), 3.46-3.24 (m, 3H), 2.79-2.62 (m, 2H), 2.58 (s, 3H), 2.37-2.27 (brm, 2H), 1.94-1.62 (brm, 3H), 1.32-1.03 (brm, 2H);

MS (ESI) m/z 339 (M-Na)$^-$.

Example 5

2-(3-Guanidinocarbonyl-2-methyl-6,7,8,9-tetrahydro-5H-cyclohepta[b]pyridin-9-ylmethyloxycarbonylamino)ethyl hydrogen sulfate (Inventive Compound 5)

In an argon atmosphere, a sulfur trioxide-pyridine complex (355 mg, 2.23 mmol) was added to a solution of Reference Compound 9 (267 mg, 0.74 mmol) in pyridine (3.7 mL), and the mixture was stirred at room temperature for 3 hours. The solvent was evaporated, then water was added, the mixture was stirred overnight, and precipitated crystals were collected by filtration, thus to obtain the title compound (261 mg, 79%) as a colorless powder.

Melting point: 229-231° C.;

IR (KBr) 3360, 3155, 2936, 2856, 1709, 1581, 1533, 1458, 1271, 1147, 1065, 1024, 894, 780, 623, 577 $cm^{-1}$;

$^1$H-NMR (300 MHz, DMSO-$d_6$) δ: 11.30 (br, 1H), 8.30-8.00 (br, 4H), 7.67 (s, 1H), 6.99 (t, J=5.0 Hz, 1H), 4.56 (dd, J=10.3, 5.2 Hz, 1H), 4.11 (dd, J=10.3, 8.5 Hz, 1H), 3.64 (t, J=6.4 Hz, 2H), 3.35-3.05 (m, 3H), 2.84-2.70 (m, 2H), 2.49 (s, 3H), 1.92-1.62 (m, 4H), 1.29-1.11 (m, 2H).

Example 6

2-(3-Guanidinocarbonyl-2-methyl-6,7,8,9-tetrahydro-5H-cyclohepta[b]pyridin-9-ylmethyloxycarbonylamino)ethyl sulfate sodium salt (Inventive Compound 6)

The Inventive Compound 5 (133 mg, 0.30 mmol) was added to distilled water (3 mL) to obtain a suspension, a 28% (w/v) sodium methoxide/methanol solution (585 µL, 0.30 mmol) was added thereto, and the mixture was stirred overnight at room temperature. After distilling off the solvent, the residue was dried under reduced pressure, thus to obtain the title compound (130 mg, 93%) as a colorless powder.

Melting point: 166-169° C.;

IR (KBr) 3421, 2930, 2846, 1701, 1656, 1600, 1523, 1458, 1413, 1339, 1258, 1163, 1069, 1023, 903, 781, 697, 633, 577 $cm^{-1}$;

$^1$H-NMR (300 MHz, DMSO-$d_6$) δ: 7.77 (s, 1H), 7.07 (t, J=5.5 Hz, 1H), 4.57 (dd, J=10.7, 4.8 Hz, 1H), 4.17 (dd, J=10.7, 9.3 Hz, 1H), 3.70 (t, J=6.0 Hz, 2H), 3.22-3.09 (m, 3H), 2.83-2.63 (m, 2H), 2.57 (s, 3H), 1.96-1.62 (m, 4H), 1.29-1.11 (m, 2H);

MS (ESI) m/z 442 (M-Na)$^-$.

Example 7

2-[2-(3-Guanidinocarbonyl-2-methyl-6,7,8,9-tetrahydro-5H-cyclohepta[b]pyridin-9-ylmethyloxycarbonylamino)ethoxy]ethyl hydrogen sulfate (Inventive Compound 7)

The title compound (160 mg, 86%) was obtained, as a colorless powder, from Reference Compound 13 (155 mg, 0.38 mmol) in the same manner as in Example 5.

Melting point: 142-144° C.;

IR (KBr) 3366, 3172, 2928, 2856, 1708, 1600, 1543, 1458, 1248, 1136, 1069, 1023, 925, 778, 641, 585 $cm^{-1}$;

$^1$H-NMR (300 MHz, DMSO-$d_6$) δ: 11.36 (brs, 1H), 8.22 (brs, 4H), 7.74 (s, 1H), 7.06 (br, 1H), 4.64-4.58 (brm, 1H), 4.20-4.14 (brm, 1H), 3.79-3.76 (m, 2H), 3.52-3.25 (m, 5H), 3.13-3.05 (m, 2H), 2.93-2.64 (m, 2H), 2.55 (s, 3H), 1.99-1.64 (m, 4H), 1.36-1.14 (m, 2H);

MS (ESI) m/z 486 (M–H)$^-$, 488 (M+H)$^+$.

Example 8

2-[2-(3-Guanidinocarbonyl-2-methyl-6,7,8,9-tetrahydro-5H-cyclohepta[b]pyridin-9-ylmethyloxycarbonylamino)ethoxy]ethyl sulfate sodium salt (Inventive Compound 8)

The title compound (584 mg, 100%) was obtained, as a colorless powder, from the Inventive Compound 7 (560 mg, 1.15 mmol) in the same manner as in Example 6.

Melting point: 168-172° C.;

IR (KBr) 3411, 2925, 2846, 1702, 1600, 1523, 1442, 1349, 1254, 1163, 1125, 1069, 1025, 930, 893, 799, 771, 716, 669, 633, 585 $cm^{-1}$;

$^1$H-NMR (300 MHz, DMSO-$d_6$) δ: 8.0-6.8 (br, 4H), 7.76 (s, 1H), 7.12 (brt, J=5.5 Hz, 1H), 4.57 (dd, J=11.0, 5.7 Hz, 1H), 4.17 (dd, J=11.0, 9.5 Hz, 1H), 3.78 (t, J=4.8 Hz, 2H), 3.50 (t, J=4.8 Hz, 2H), 3.38 (t, J=6.8 Hz, 2H), 3.25-3.17 (m, 1H), 3.14-3.08 (m, 2H), 2.84-2.63 (m, 2H), 2.57 (s, 3H), 1.96-1.62 (m, 4H), 1.29-1.15 (m, 2H);

MS (ESI) m/z 486 (M-Na)$^-$, 510 (M+H)$^+$.

Example 9

17-(3-Guanidinocarbonyl-2-methyl-6,7,8,9-tetrahydro-5H-cyclohepta[b]pyridin-9-ylmethyloxycarbonylamino)-3,6,9,12,15-pentaoxaheptadecan-1-yl hydrogen sulfate (Inventive Compound 9)

In an argon atmosphere, the title compound (100 mg, 59%) was obtained, as a colorless amorphous material, from Reference Compound 16 (149 mg, 0.26 mmol) in the same manner as in Example 5.

IR (KBr) 3367, 2924, 2865, 1702, 1600, 1544, 1458, 1249, 1144, 1103, 1013, 939, 771, 679 $cm^{-1}$;

$^1$H-NMR (300 MHz, CD$_3$OD) δ: 7.73 (s, 1H), 4.78-4.73 (m, 1H), 4.27 (dd, J=10.6, 7.8 Hz, 1H), 4.07 (t, J=4.8 Hz, 2H), 3.70-3.23 (m, 23H), 2.92-2.89 (m, 2H), 2.62 (s, 3H), 2.04-1.76 (m, 4H), 1.50-1.30 (m, 2H);

MS (ESI) m/z 664 (M+H)$^+$, 662 (M–H)$^-$.

Example 10

17-(3-Guanidinocarbonyl-2-methyl-6,7,8,9-tetrahydro-5H-cyclohepta[b]pyridin-9-ylmethyloxycarbonylamino)-3,6,9,12,15-pentaoxaheptadecan-1-yl sulfate sodium salt (Inventive Compound 10)

The title compound (68.2 mg, 69%) was obtained, as a colorless amorphous material, from the Inventive Compound 9 (95.7 mg, 0.14 mmol) in the same manner as in Example 6.

IR (KBr) 3418, 2923, 2865, 1704, 1637, 1599, 1524, 1455, 1349, 1254, 1099, 1023, 945, 776 $cm^{-1}$;

$^1$H-NMR (300 MHz, CD$_3$OD) δ: 7.62 (s, 1H), 4.70 (dd, J=11.0, 6.1 Hz, 1H), 4.31 (dd, J=11.0, 9.8 Hz, 1H), 4.13-4.11 (m, 2H), 3.72-3.51 (m, 20H), 3.40-3.25 (m, 3H), 2.85-2.81 (m, 2H), 2.58 (s, 3H), 2.02-1.75 (m, 4H), 1.52-1.36 (m, 2H);

MS (ESI) m/z 686 (M+H)$^+$, 664 (M-Na+2H)$^+$, 662 (M-Na)$^-$.

Example 11

2-(3-Guanidinocarbonyl-2-methyl-6,7,8,9-tetrahydro-5H-cyclohepta[b]pyridin-9-ylmethyloxycarbonylamino)-[N-(2-sulfoxyethyl)]ethyl hydrogen sulfate (Inventive Compound 11)

Bis-(2-sulfoxyethyl)amine monopotassium salt (271 mg, 0.50 mmol) and Reference Compound 11 (170 mg, 0.56 mmol) were added to DMF (5 mL), triethylamine (279 μL, 2.0 mmol) was added thereto, and the resulting mixture was stirred at room temperature for 17 hours. The solvent was evaporated under reduced pressure, a saturated aqueous solution of sodium hydrogen carbonate was added to the residue, and then the mixture was washed with ethyl acetate. The aqueous layer was neutralized with 6 mol/L hydrochloric acid, and then the aqueous layer was combined with the organic layer. The solvent was evaporated, and the residue was purified by silica gel column chromatography (chloroform:methanol=10:1 to 6:1), thus to obtain the title compound (117 mg, 41%) as a colorless amorphous material.

IR (neat) 3420, 3181, 2930, 2856, 1721, 1684, 1646, 1581, 1487, 1455, 1432, 1245, 1153, 1064, 1016, 995, 904, 769 cm$^{-1}$;

$^1$H-NMR (300 MHz, CD$_3$OD) δ: 7.59 (s, 1H), 4.84-4.77 (m, 1H), 4.29 (dd, J=10.6, 4.8 Hz, 1H), 4.09-4.05 (m, 2H), 3.64-3.42 (m, 7H), 2.91-2.85 (m, 2H), 2.60 (s, 3H), 2.01-1.80 (m, 4H), 1.54-1.43 (m, 2H);

MS (ESI) m/z 568 (M+H)$^+$, 566 (M−H)$^-$, 282.5 (M−2H)$^{2-}$.

Example 12

2-Deoxy-1,4:3,6-dianhydro-2-(3-guanidinocarbonyl-2-methyl-6,7,8,9-tetrahydro-5H-cyclohepta[b]pyridin-9-ylmethyloxycarbonylamino)-D-glucitol-5-yl hydrogen sulfate (Inventive Compound 12)

A sulfur trioxide-pyridine complex (213 mg, 1.34 mmol) was added to a solution of Reference Compound 18 (200 mg, 0.45 mmol) in DMF (4.5 mL), and the mixture was stirred for 2 hours. The solvent was evaporated under reduced pressure, and the residue was purified by C$_{18}$ silica gel chromatography (water to 50% methanol), thus to obtain the title compound (195 mg, 83%) as a colorless powder.

Melting point: 204-205° C.;

IR (KBr) 3368, 2929, 2856, 1712, 1595, 1543, 1458, 1250, 1150, 1038, 1011, 893, 780, 618, 580 cm$^{-1}$;

$^1$H-NMR (300 MHz, DMSO-d$_6$) δ: 11.34 (br, 1H), 8.12 (br, 4H), 7.74 (s, 1H), 7.45 (d, J=5.1 Hz, 1H), 4.63 (dd, J=10.8, 6.1 Hz, 1H), 4.46 (s, 2H), 4.30 (s, 1H), 4.18 (dd, J=10.3, 8.6 Hz, 1H), 3.82-3.63 (m, 5H), 3.45 (dd, J=8.4, 7.7 Hz, 1H), 2.92-2.72 (m, 2H), 2.54 (s, 3H), 1.97-1.68 (m, 4H), 1.34-1.14 (m, 2H);

MS (ESI) m/z 528 (M+H)$^+$.

Example 13

2-Deoxy-1,4:3,6-dianhydro-2-(3-guanidinocarbonyl-2-methyl-6,7,8,9-tetrahydro-5H-cyclohepta[b]pyridin-9-ylmethyloxycarbonylamino)-D-glucitol-5-yl sulfate sodium salt (Inventive Compound 13)

The title compound (598 mg, 82%) was obtained, as a colorless amorphous material, from the Inventive Compound 12 (704 mg, 1.34 mmol) in the same manner as in Example 6.

IR (KBr) 3422, 2927, 2855, 1703, 1637, 1602, 1523, 1439, 1417, 1350, 1257, 1094, 1040, 1011, 891, 801, 620, 585 cm$^{-1}$;

$^1$H-NMR (300 MHz, DMSO-d$_6$+D$_2$O) δ: 7.76 (s, 1H), 4.60 (dd, J=10.6, 3.7 Hz, 1H), 4.53-4.47 (m, 2H), 4.32 (s, 1H), 4.17 (t, J=9.8 Hz, 1H), 3.85-3.78 (m, 3H), 3.66 (d, J=9.2 Hz, 1H), 3.48-3.38 (m, 2H), 3.25-3.16 (m, 1H), 2.82-2.65 (m, 2H), 2.56 (s, 3H), 1.94-1.61 (m, 4H), 1.29-1.12 (m, 2H);

MS (ESI) m/z 526 (M-Na)$^-$.

The compound represented by Formula (1) of the present invention has a structure in which the hydroxyl group on the methyl group at the 9-position of 9-hydroxymethylcyclohepta[b]pyridine-3-carbonylguanidine derivative is converted to a specific substituent. A representative compound of the invention was evaluated for the NHE inhibitory effect, toxic effects on the central nervous system and the like, in comparison with the corresponding 9-hydroxymethylcyclohepta[b]pyridine-3-carbonylguanidine derivative, according to the following Test Examples. In order to make comparison with the present invention, compounds obtained by introducing a phosphoric acid group instead of the group represented by R$^1$ in the Formula (1) of the present invention, compounds resulting from changing the substitution position for R$^1$, and the like were also evaluated as such.

The following compounds were evaluated as the test compounds.

[Test Compounds]

3-Guanidinocarbonyl-2-methyl-6,7,8,9-tetrahydro-5H-cyclohepta[b]pyridin-9-ylmethyl sulfate sodium salt (Inventive Compound 2).

3-Guanidinocarbonyl-2-methyl-6,7,8,9-tetrahydro-5H-cyclohepta[b]pyridin-9-ylmethanesulfonic acid sodium salt (Inventive Compound 4).

2-(3-Guanidinocarbonyl-2-methyl-6,7,8,9-tetrahydro-5H-cyclohepta[b]pyridin-9-ylmethyloxycarbonylamino)ethyl sulfate sodium salt (Inventive Compound 6).

2-[2-(3-Guanidinocarbonyl-2-methyl-6,7,8,9-tetrahydro-5H-cyclohepta[b]pyridine-9-ylmethyloxycarbonylamino)ethoxy]ethyl hydrogen sulfate (Inventive Compound 7).

2-[2-(3-Guanidinocarbonyl-2-methyl-6,7,8,9-tetrahydro-5H-cyclohepta[b]pyridine-9-ylmethyloxycarbonylamino)ethoxy]ethyl sulfate sodium salt (Inventive Compound 8).

17-(3-guanidinocarbonyl-2-methyl-6,7,8,9-tetrahydro-5H-cyclohepta[b]pyridin-9-ylmethyloxycarbonylamino)-3,6,9,12,15-pentaoxaheptadecan-1-yl hydrogen sulfate sodium salt (Inventive Compound 10).

2-Deoxy-1,4:3,6-dianhydro-2-(3-guanidinocarbonyl-2-methyl-6,7,8,9-tetrahydro-5H-cyclohepta[b]pyridin-9-ylmethyloxycarbonylamino)-D-glucitol-5-yl hydrogen sulfate (Inventive Compound 12).

3-Guanidinocarbonyl-2-methyl-6,7,8,9-tetrahydro-5H-cyclohepta[b]pyridin-9-ylmethyl phosphate disodium salt (Reference Compound 20).

3-Guanidinocarbonyl-6,7,8,9-tetrahydro-5H-cyclohepta[b]pyridin-2-ylmethyl hydrogensulfate (Reference Compound 22).

3-Guanidinocarbonyl-2-methyl-6,7,8,9-tetrahydro-5H-cyclohepta[b]pyridin-5-yl hydrogen sulfate (Reference Compound 23).

9-Hydroxymethyl-2-methyl-6,7,8,9-tetrahydro-5H-cyclohepta[b]pyridine-3-carbonylguanidine methanesulfonic acid salt (methanesulfonic acid salt of Reference Compound 4 (Example 40 of WO98/39300): Control Compound)

Test Example 1

NHE Inhibitory Effect Test

The NHE inhibitory activity was measured according to the method by Scholz et al. [British Journal of Pharmacology, Vol. 109, p. 562-568 (1993)], taking the swelling of rat platelets induced by sodium propionate as an index.

Under etherization, blood was collected (8 mL) from the abdominal aorta of a Wistar rat, and 1 mL of a citrate dextrose solution as an anticoagulant was added. The blood sample was immediately centrifuged at 90×g for 10 minutes, and then the collected supernatant was taken as platelet-rich plasma. Subsequently, to 250 μL of a 140 mM sodium propionate buffer solution containing the test compound dissolved in dimethylsulfoxide (pH 6.7, final dimethylsulfoxide concentration 1%), the platelet-rich plasma prepared in the above (number of platelet; $10 \times 10^6 / 50$ μL) was added, and the decrease in the absorbance associated with the swelling of platelets was measured over time with a Hematracer (NKK Corp.).

The rate of decrease in the absorbance at 20 seconds after the addition of the platelet-rich plasma was taken as the NHE activity, and the inhibitory activity of the respective compounds was expressed as a relative activity, while the action obtained upon addition of 300 μM of Amiloride was taken as 100% inhibition.

In addition, the test results were obtained by calculating the concentration at which the inhibitory activity of the test compound becomes 50% ($IC_{50}$ value), by a Probit method. The $IC_{50}$ values for the NHE inhibitory activity of these test compounds are presented in Table 1.

TABLE 1

| Test Compound | $IC_{50}$ value |
|---|---|
| Inventive Compound 2 | $1.43 \times 10^{-7}$ M |
| Inventive Compound 4 | $2.11 \times 10^{-7}$ M |
| Inventive Compound 6 | $1.42 \times 10^{-7}$ M |
| Inventive Compound 7 | $3.13 \times 10^{-7}$ M |
| Inventive Compound 10 | $2.91 \times 10^{-7}$ M |
| Inventive Compound 12 | $2.27 \times 10^{-7}$ M |
| Reference Compound 20 | $6.62 \times 10^{-7}$ M |
| Reference Compound 22 | $>1.00 \times 10^{-4}$ M |
| Reference Compound 23 | $3.71 \times 10^{-5}$ M |
| Control Compound | $3.34 \times 10^{-8}$ M |

Test Example 2

Reperfusion-Induced Arrhythmia Inhibitory Action Test

Subsequently, in evaluation of the in vivo NHE inhibitory action, the effect of the test compound on reperfusion-induced arrhythmia upon myocardial ischemia was evaluated according to the method of Aihara et al. [European Journal of Pharmacology, Vol. 404, p. 221-229 (2000)]. Under anesthesia using pentobarbital sodium (60 mg/kg, intraperitoneal administration), cannulae were inserted into trachea, femoral vein and carotid artery of male SD rats (weeks old) for artificial ventilation, drug administration and blood pressure measurement, respectively. The blood pressure was measured using a strain pressure amplifier via a pressure transducer, while the heart rate was measured from the blood pressure pulse wave using a cardiotachometer. Furthermore, an electrocardiogram (lead II) was measured from the electrodes attached to each four limbs. Next, under artificial ventilation, left thoracotomy was performed and a snare (5-0 nylon) was loosely placed around a blood vessel which was about 3 mm apart from the origin of the left coronary artery. Thereafter, it was confirmed that arrhythmia was not occurred for 10 minutes, and then the snare was fastened to induce local myocardial ischemia. Furthermore, after 4 minutes of myocardial ischemia, the compound was intravenously administered for 1 minute, and after 5 minutes of myocardial ischemia, the snare was loosened, then the arrhythmia occurred after reperfusion was recorded and analyzed with an arrhythmia analyzer (Softron Co., Ltd.), thereby the anti-arrhythmic action of the compound was evaluated. The test compounds were respectively dissolved in physiological saline at a concentration of 3.62 mmol/L, and 4 to 5 animals in each group were respectively administered at 1 mL/kg of the compound. The control group was administered with physiological saline.

With regard to the ventricular fibrillation (Vf) which occurred within 10 minutes after reperfusion (in the cases of halfway death, up to the time point where cardiac arrest was confirmed), arrhythmia analysis was performed according to the Guidelines for Lambeth Convention [Cardiovascular research, Vol. 22, p. 447-455, 1988], and evaluation was made in terms of the frequency of Vf occurrence, cumulative duration time of Vf, and the mortality.

The frequency of Vf occurrence, cumulative duration of Vf, and the mortality for the respective test compounds are presented in Table 2.

TABLE 2

| | | Frequency of Vf occurrence (%) | Cumulative duration of Vf (second) | Mortality (%) |
|---|---|---|---|---|
| Group administered with compound of present invention | Inventive Compound 2 | 40 | 13.7 | 20 |
| | Inventive Compound 4 | 60 | 25.3 | 0 |
| | Inventive Compound 6* | 20 | 23.3 | 0 |
| | Inventive Compound 7 | 40 | 15.4 | 0 |
| | Inventive Compound 10 | 67 | 11.1 | 0 |
| | Inventive Compound 12 | 0 | 0.0 | 0 |
| Group administered with reference material | Control compound | 50 | 30.2 | 25 |
| | Reference Compound 20 | 80 | 46.8 | 40 |
| Non-drug-administered group (administered with physiological saline) | | 75 | 96.3 | 75 |

*The concentration was 1.09 mmol/L, and administration of 1 mL/kg was performed in 5 animals.

The compound of the present invention exhibited a high NHE inhibitory action both in vitro and in vivo. Although the activity in vitro was slightly lower as compared with the control compound, the NHE inhibitory activity was still strong. Meanwhile, unlike the present invention, the Reference Compound 22 and 23, in which sulfoxy groups were introduced at the 5-position and 2-position of the cyclohepta[b]pyridine ring respectively, showed significant lowering in the activity. Moreover, for reperfusion-induced arrhythmia, the compound of the present invention greatly shortened the cumulative duration of Vf and lowered the mortality, thus effects of the inventive compound were comparable to or greater than those of the control compound.

Test Example 3

Metabolic Stability Test in Rat

The compound represented by Formula (1) of the present invention has a structure in which the hydroxyl group on the 9-position of a 9-hydroxymethyl-cyclohepta[b]pyridine-3-carbonylguanidine derivative is converted to a specific substituent. However, if the compound is metabolized in vivo to remove the specific substituent from the compound, there may be generated the original 9-hydroxymethyl-cyclohepta[b]pyridine-3-carbonylguanidine derivative, which has toxic effects on the central nervous system. Thus, the inventive compounds as synthesized in Examples were administered in vivo to study whether the control compound, which was the corresponding 9-hydroxymethyl product, was generated.

Male SD rats (7 weeks old) were administered at 1 mg/kg (an amount calculated excluding salts) of the control compound, an equivalent amount of the Inventive Compound 2, 4, 6, 7 or 12, or Reference Compound 20, through the tail vein. After administration, about 0.2 mL of blood samples were collected after 5, 15, 30, 60 and 120 minutes, and the blood samples were centrifuged at 4° C. at a speed of rotation of 15000 for 15 minutes, thus to separate the supernatant plasma. The concentration of the control compound in the plasma was measured by LC/MS/MS. The measurement results were shown as +++ when the detected plasma concentration of the control compound is 200 ng/mL or greater; ++ for more than 100 ng/mL and less than 200 ng/mL; + for more than 20 ng/mL and less than 100 ng/mL; and – for less than 20 ng/mL or no detection. The results are presented in Table 3.

TABLE 3

|  | After 5 min | After 15 min | After 30 min | After 60 min | After 120 min |
|---|---|---|---|---|---|
| Inventive Compound 2 | – | – | – | – | – |
| Inventive Compound 4 | – | – | – | – | – |
| Inventive Compound 6 | – | – | – | – | – |
| Inventive Compound 7 | – | – | – | – | – |
| Inventive Compound 12 | – | – | – | – | – |
| Reference compound 20 | +++ | ++ | + | + | – |
| Control Compound | +++ | ++ | + | + | – |

For the Inventive Compounds 2, 4, 6, 7 and 12, the control compound was not detected at any time point, and it was found that the Inventive Compounds do not decompose into the Control Compound in vivo, which indicates a possibility of reduced toxic effects of the compounds of the present invention on the central nervous system was suggested. Meanwhile, the Reference Compound 20 which was a phosphoric acid derivative was rapidly degraded to the Control Compound after administration, and thus, it was conceived that the Reference Compound 20 showed the same toxic effects on the central nervous system as those of the Control Compound.

Test Example 4

Toxicity Test with 2-Days Repeated Intraperitoneal Administration in Mouse

For three male mice in each group, 300 mg/kg of the Control Compound (an amount calculated excluding salts), or an equivalent amount of the Inventive Compound 2, 4, 6, 7 or 12 were intraperitoneally administered once a day for 2 days, and a histopathological tests were performed. The Control Compound, and the Inventive Compounds 2, 4 and 6 were suspended in a 0.5% tragacanth gum solution, and the Inventive Compound 7 was suspended in a 10 DMSO-containing 0.5% tragacanth gum solution, while the Inventive Compound 12 was suspended in olive oil. For the histopathological test, in order to make a more thorough examination of central nervous toxicity, the brain was examined after whole body was subjected to perfusion fixation with a 4% formaldehyde in neutral phosphate buffer as a fixing solution using a liquid transporting pump under pentobarbital sodium anesthesia.

In the pathological test, vacuolation was recognized in the cerebellar nuclei and vestibular nuclei in the group administered with the Control Compound, but for the groups administered with the Inventive Compounds 2, 4, 6, 7 and 12, any histologic finding which could be caused by drug administration was not recognized.

From the results, it was confirmed that the toxicity of the Inventive Compounds 2, 4, 6, 7 and 12 on the central nervous system was obviously reduced as compared to the Control Compound.

Test Example 5

Toxicity Test after 4-Days Repeated Intravenous Administration in Beagle Dogs

With one male and one female dogs in each group, 30 mg/kg of the Control Compound dissolved in physiological saline (an amount calculated excluding salts), or an equivalent amount of the Inventive Compound 2, 4, 6 or 8 was repeatedly administered intravenously once a day for 4 days, and general symptom observation and pharmacological histopathologic examination were performed. For the histopathologic examination, in order to perform a more thorough examination of the central nervous toxicity, only the brain was examined after whole body was subjected to perfusion fixation with a 4% formaldehyde in neutral phosphate buffer as a fixing solution using a liquid transporting pump under pentobarbital sodium anesthesia.

As a result, in a general condition, vomiting, salivation, and decreases in locomotor activity, staggering gait and ananastasia were recognized in the group administered with the Control Compound. On the other hand, in the groups administered with the Inventive Compounds 2, 4, 6 and 8, only vomiting was recognized. In the pathologic examination, necrosis/chromatolysis of nerve cells, swelling of axons and vacuolation of myelin sheath were recognized in the cerebellar nuclei and vestibular nucleus of the group administered with the Control Compound. In the groups administered with the Inventive Compounds 2, 4, 6 and 8, any histologic finding which could be caused by drug administration was not recognized in both male and female dogs.

From the above results, it was confirmed that the toxicities of the Inventive Compounds 2, 4, 6 and 8 on the central nervous system were obviously reduced as compared to the Control Compound.

Test Example 6

Comparative Test for Transferability to the Brain in Rat

To male SD rats (6 weeks old), the Control Compound or the Inventive Compound 2 was administered through the tail vein in an amount of 50 mg/kg. After administration, whole blood samples were collected over time from the abdominal aorta under etherization, and the brain tissues were extracted immediately. The brain tissues were lightly washed off to remove the blood attached around with physiological saline, and subsequently the tissues were frozen in liquid nitrogen and preserved at −30° C. until analyzed. The blood was centrifuged at 4° C. at a rotation speed of 15000 for 15 minutes to separate the supernatant plasma, and was preserved at −30° C. until analyzed. The brain tissues were thawed by standing at ambient temperature, and then the wet weight was measured. Distilled water was added in an amount five times of the wet weight, and a suspension was prepared using a Polytron homogenizer. The measurement of the test compound concentration in the plasma and the brain tissues was performed by LC/MS/MS. The transferability of the drug to the brain was calculated by dividing the drug concentration in the brain tissues by the plasma concentration obtained at the same time. The test results are presented in Table 4.

TABLE 4

| Test Compound | Concentration Intracerebral/Plasma | |
| --- | --- | --- |
|  | After 15 min | After 30 min |
| Inventive Compound 2 | 0.29 | N.D.* |
| Control Compound | 1.64 | 2.33 |

*N.D. The intracerebral concentration was not detected.

Compared with the Control Compound, the Inventive Compound 2 was confirmed to have decreased transferability to the brain tissues. From this, the decreased toxic effects on the central nervous system were proved.

Preparation Example 1

Production of Tablet 5 g of the Inventive Compound 2, 125 g of lactose, 40 g of corn starch and 20 g of crystalline cellulose were mixed, and 6 g of hydroxypropylcellulose in the form of a 100 ethanol solution was added to the mixture. The mixture was kneaded, granulated, and extruded through a screen with a diameter of 8 mm to prepare granules. After drying the granules, 4 g of magnesium stearate was added, and the mixture was compressed to produce tablets having a weight of 200 mg, each tablet containing 5 mg of the Inventive Compound 2.

Preparation Example 2

Production of Injectable Preparation or Solution 50 mg of the Inventive Compound 2 and 900 mg of sodium chloride were dissolved in 90 mL of water for injection, and then 1 mmol/L hydrochloric acid was added to adjust the solution to pH 7.0. More water for injection was added to make up to a total volume of 100 mL. This solution was sterilized by filtration, and filled into glass ampoules in an amount of 2 mL each, thus to produce an injectable preparation (solution) containing 1 mg of the Inventive Compound 2 per ampoule.

Preparation Example 3

Production of Suppository

Witepsol H-15 was heated to melt, the Inventive Compound 2 was added thereto to a concentration of 10 mg/mL, and the mixture was homogenized. This mixture was injected into plastic containers for suppositories in an amount of 2 mL each, and cooled to produce suppositories, each containing 20 mg of the Inventive Compound 2 per container.

Preparation Example 4

Production of Eye-Drop 50 mg of the Inventive Compound 2, 0.1 g of sodium dihydrogen phosphate•dihydrate, 0.9 g of sodium chloride and 5 mg of benzalkonium chloride were dissolved in 80 mL of purified water. A 0.1 mol/L aqueous solution of sodium hydroxide was added thereto, the mixture was adjusted to pH 7.0, and purified water was added thereto to make up to a total volume of 100 mL. This solution was sterilized by filtration, and then filled into eye-drop containers made of polypropylene in an amount of 5 mL each, thus to produce an eye-drop containing the Inventive Compound 2 at a concentration of 0.05%.

The invention claimed is:

1. A cyclohepta[b]pyridine-3-carbonylguanidine compound represented by Formula (I):

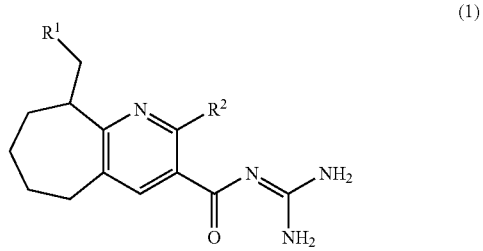

wherein $R^1$ represents a group selected from a sulfo group, a sulfoxy group, —OCONH—$(CH_2CH_2O)_n$—$SO_3H$ and the following formulas:

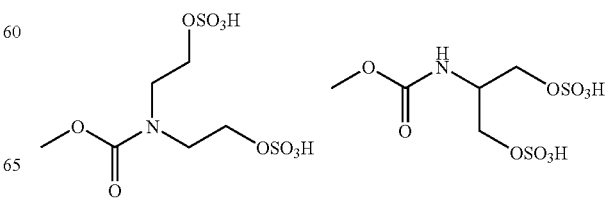

-continued

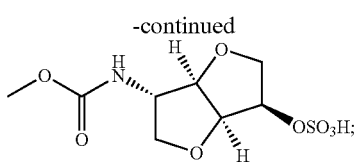

R² represents a halogen atom, a lower alkyl group or a lower alkoxy group; and n represents an integer from 1 to 10,
or a pharmaceutically acceptable salt thereof.

2. The cyclohepta[b]pyridine-3-carbonylguanidine compound according to claim 1, or a pharmaceutically acceptable salt thereof, selected from the group consisting of:
- 3-guanidinocarbonyl-2-methyl-6,7,8,9-tetrahydro-5H-cyclohepta[b]pyridin-9-ylmethyl hydrogen sulfate,
- 3-guanidinocarbonyl-2-methyl-6,7,8,9-tetrahydro-5H-cyclohepta[b]pyridin-9-ylmethanesulfonic acid,
- 2-(3-guanidinocarbonyl-2-methyl-6,7,8,9-tetrahydro-5H-cyclohepta[b]pyridin-9-ylmethyloxycarbonylamino) ethyl hydrogen sulfate,
- 2-[2-(3-guanidinocarbonyl-2-methyl-6,7,8,9-tetrahydro-5H-cyclohepta[b]pyridin-9-ylmethyloxycarbonylamino)ethoxy]ethyl hydrogen sulfate,
- 17-(3-guanidinocarbonyl-2-methyl-6,7,8,9-tetrahydro-5H-cyclohepta[b]pyridin-9-ylmethyloxycarbonylamino)-3,6,9,12,15-pentaoxaheptadecan-1-yl hydrogen sulfate,
- 2-(3-guanidinocarbonyl-2-methyl-6,7,8,9-tetrahydro-5H-cyclohepta[b]pyridin-9-ylmethyloxycarbonylamino)-[N-(2-sulfoxyethyl)]ethyl hydrogen sulfate, and
- 2-deoxy-1,4:3,6-dianhydro-2-(3-guanidinocarbonyl-2-methyl-6,7,8,9-tetrahydro-5H-cyclohepta[b]pyridine-9-ylmethyloxycarbonylamino)-D-glucitol-5-yl hydrogen sulfate.

3. The cyclohepta[b]pyridine-3-carbonylguanidine compound according to claim 1, or a pharmaceutically acceptable salt thereof, selected from the group consisting of:
- 3-Guanidinocarbonyl-2-methyl-6,7,8,9-tetrahydro-5H-cyclohepta[b]pyridin-9-ylmethyl hydrogen sulfate,
- 3-guanidinocarbonyl-2-methyl-6,7,8,9-tetrahydro-5H-cyclohepta[b]pyridin-9-ylmethanesulfonic acid,
- 2-(3-guanidinocarbonyl-2-methyl-6,7,8,9-tetrahydro-5H-cyclohepta[b]pyridin-9-ylmethyloxycarbonylamino) ethyl hydrogen sulfate, and
- 2-[2-(3-guanidinocarbonyl-2-methyl-6,7,8,9-tetrahydro-5H-cyclohepta[b]pyridin-9-ylmethyloxycarbonylamino)ethoxy]ethyl hydrogen sulfate, or a pharmaceutically acceptable salts salt thereof.

4. A medicine comprising the cyclohepta[b]pyridine-3-carbonylguanidine compound according to any one of claims 1 to 3, or a pharmaceutically acceptable salt thereof as an active ingredient.

5. An Na⁺/H⁺ exchanger inhibitor, comprising the cyclohepta[b]pyridine-3-carbonylguanidine compound according to any one of claims 1 to 3, or a pharmaceutically acceptable salt thereof as an active ingredient.

6. A pharmaceutical composition comprising the cyclohepta[b]pyridine-3-carbonylguanidine compound according to any one of claims 1 to 3 or a pharmaceutically acceptable salt thereof, and a pharmaceutically acceptable carrier.

* * * * *